(12) United States Patent
Wang et al.

(10) Patent No.: US 10,941,166 B2
(45) Date of Patent: Mar. 9, 2021

(54) CRYSTALLINE HIGH DEGREE OF CONDENSATION TITANIUM-BASED INORGANIC-ORGANIC HYBRID SOLID MOF MATERIAL, METHOD FOR PREPARING SAME AND USES THEREOF

(71) Applicants: CENTRE NATIONAL DE LA RECHERCHE SCIENTIFIQUE, Paris (FR); UNIVERSITÉ DE VERSAILLES—SAINT-QUENTIN-EN-YVELINES, Versailles (FR)

(72) Inventors: Sujing Wang, Versailles (FR); Christian Serre, Plaisir (FR); Nathalie Guillou, Chavenay (FR); Nathalie Steunou, Frémécourt (FR)

(73) Assignees: CENTRE NATIONAL DE LA RECHERCHE SCIENTIFIQUE, Paris (FR); UNIVERSITÉ DE VERSAILLES SAINT QUENTIN EN YVELINES, Versailles (FR)

( * ) Notice: Subject to any disclaimer, the term of this patent is extended or adjusted under 35 U.S.C. 154(b) by 0 days.

(21) Appl. No.: 16/308,686

(22) PCT Filed: Jun. 8, 2017

(86) PCT No.: PCT/EP2017/063908
§ 371 (c)(1),
(2) Date: Dec. 10, 2018

(87) PCT Pub. No.: WO2017/211923
PCT Pub. Date: Dec. 14, 2017

(65) Prior Publication Data
US 2019/0248814 A1 Aug. 15, 2019

(30) Foreign Application Priority Data
Jun. 10, 2016 (EP) .................................. 16305692

(51) Int. Cl.
*C07F 7/28* (2006.01)
*B01J 20/22* (2006.01)
(Continued)

(52) U.S. Cl.
CPC ................ *C07F 7/28* (2013.01); *A61K 47/24* (2013.01); *B01J 20/226* (2013.01);
(Continued)

(58) Field of Classification Search
None
See application file for complete search history.

(56) References Cited

U.S. PATENT DOCUMENTS

2009/0198079 A1    8/2009 Schubert
2014/0200361 A1    7/2014 Lee

FOREIGN PATENT DOCUMENTS

WO    2009133278 A1    11/2009
WO    2011099967 A1    8/2011
(Continued)

OTHER PUBLICATIONS

Galo J. de A. A. Soler-Illia, "Design of meso-structured titanium oxo based hybrid organic-inorganic networks", New Journal of Chemistry, vol. 25, No. 1, Jan. 1, 2001, pp. 156-165, XP0002982497.
(Continued)

*Primary Examiner* — Clinton A Brooks
(74) *Attorney, Agent, or Firm* — Cantor Colburn LLP

(57) ABSTRACT

The present invention relates to a water-stable Titanium-based metal-organic framework (MOF) material having a high degree of condensation, i.e. an oxo to Ti ratio (or oxo to metal ratio, in the case of doped Ti-based MOFs) >1.0; a process of preparing same and uses thereof, particularly for heterogeneously catalyzed chemical reactions, for gas storage/separation/purification, for information storage, laser printing or as an oxygen indicator, or as proton conductive
(Continued)

material (fuel cells), optoelectronic material (photovoltaic cells including Grätzel cells), as a matrix for encapsulating active principles (medicaments, cosmetics), or else as sensing material.

24 Claims, 8 Drawing Sheets

(51) Int. Cl.
| | | |
|---|---|---|
| B01J 31/16 | (2006.01) | |
| F17C 11/00 | (2006.01) | |
| C07F 7/00 | (2006.01) | |
| B01J 31/22 | (2006.01) | |
| B01J 35/00 | (2006.01) | |
| A61K 47/24 | (2006.01) | |
| B01J 20/28 | (2006.01) | |
| B01J 20/30 | (2006.01) | |
| B01J 35/10 | (2006.01) | |
| B01J 37/04 | (2006.01) | |
| C09K 9/02 | (2006.01) | |
| H01M 8/1016 | (2016.01) | |

(52) U.S. Cl.
CPC ... *B01J 20/28061* (2013.01); *B01J 20/28064* (2013.01); *B01J 20/28066* (2013.01); *B01J 20/28071* (2013.01); *B01J 20/28073* (2013.01); *B01J 20/28076* (2013.01); *B01J 20/3085* (2013.01); *B01J 31/1691* (2013.01); *B01J 31/2226* (2013.01); *B01J 31/2239* (2013.01); *B01J 35/004* (2013.01); *B01J 35/1019* (2013.01); *B01J 35/1023* (2013.01); *B01J 35/1028* (2013.01); *B01J 35/1038* (2013.01); *B01J 35/1042* (2013.01); *B01J 35/1047* (2013.01); *B01J 37/04* (2013.01); *C07F 7/003* (2013.01); *C09K 9/02* (2013.01); *F17C 11/00* (2013.01); *H01M 8/1016* (2013.01); *B01J 2531/0216* (2013.01); *B01J 2531/46* (2013.01); *C09K 2211/183* (2013.01); *H01M 2300/0065* (2013.01); *Y02E 60/32* (2013.01)

(56) References Cited

FOREIGN PATENT DOCUMENTS

| WO | 2016033086 A1 | 3/2016 |
| WO | 2016088106 A1 | 6/2016 |

OTHER PUBLICATIONS

International Search Report for corresponding application PCT/EP2017/063908 filed Jun. 8, 2017; dated Sep. 11, 2017.
Laurence Rozes, "Titanium oxo-clusters: precursors for a Lego-like construction of nanostructured hybrid materials", Chemical Society Reviews, vol. 40, No. 2, Jan. 1, 2011, p. 1006, XP0555326153.
Michal Sabo, "Titanium terephthalate (TT-1) hybrid materials with high specific surface area", Journal of Materials Chemistry, vol. 16, No. 24, Jan. 1, 2006, pp. 2354-2357, XP055326155.
Weimin Xuan, "A Chiral porous metallosalan-organic framework containing titanium-oxo clusters for enantioselective catalytic sulfoxidation", Chemical Science, RSC Publishing, 2013, vol. 4, No. 8, XP055326139.
Written Opinion of the International Searching Authority PCT/EP2017/063908 filed Jun. 8, 2017; dated Sep. 11, 2017.

| LT structure | | | | HT structure | | | |
|---|---|---|---|---|---|---|---|
| $Ti_{24}O_{30}L_6(formate)_{12} \cdot 14.4H_2O$ <br> FW 4398.94 g/mol <br> space group: *P6/mmm* (191) hexagonal <br> $a = b = 22.5956(4)$ Å, $c = 12.3064(3)$ Å <br> $V = 5441.38(20)$ Å$^3$ | | | | $Ti_{24}O_{36}L_6$ <br> FW 3766.57 g/mol <br> space group: *P6/mmm* (191) hexagonal <br> $a = b = 21.8156(2)$ Å, $c = 11.9854(1)$ Å <br> $V = 4939.89(9)$ Å$^3$ | | | |
| atom | x | y | z | atom | x | y | z |
| Ti1 | 0.5633(2) | 0.28166(11) | 0.2502(4) | Ti1 | 0.56120(15) | 0.28060(7) | 0.15033(20) |
| Ti2 | 0.5193(2) | 0.1953(2) | 0 | Ti2 | 0.61285(7) | 0.22571(15) | 0.64875(22) |
| O1 | 0.4975(7) | 0.1297(4) | 0.8799(10) | O1 | 0.70121(27) | 0.51952(27) | 0.17621(43) |
| O2 | 0.4905(7) | 0.1843(5) | 0.7360(9) | O2 | 0.62840(27) | 0.48754(30) | 0.32313(42) |
| O4 | 0.5294(6) | 0.2647(3) | 0.0995(11) | O3 | 0.57767(37) | 0.28883(19) | 0.33614(59) |
| O5 | 0.5687(8) | 0.2844(4) | 0.5930(11) | O4 | 0.62203(20) | 0.24406(39) | 0.82586(56) |
| O6 | 0.6286(3) | 0.2571(6) | 0.23487 | O5 | 0.56026(55) | 0.28013(28) | 0 |
| O7 | 0.4217(7) | 0.1561(7) | 0 | O6 | 0.60815(28) | 0.21629(55) | 0.5 |
| C1 | 0.2925(4) | 0 | 0.5 | C1 | 0.74003(41) | 0.74003(41) | 0 |
| C2 | 0.3310(4) | 0 | 0.5991(4) | C2 | 0.69764(34) | 0.69764(34) | 0.1017(6) |
| C3 | 0.3806(5) | 0.0628(2) | 0.6461(5) | C3 | 0.70131(28) | 0.63863(25) | 0.13618(52) |
| C4 | 0.4171(5) | 0.0628(2) | 0.7400(7) | C4 | 0.65771(22) | 0.59344(22) | 0.22336(57) |
| C5 | 0.4639(5) | 0 | 0.7869(8) | C5 | 0.60190(37) | 0.60190(37) | 0.26126(70) |
| C6 | 0.4695(7) | 0.1291(3) | 0.7896(9) | H1 | 0.79561 | 0.74856 | 0 |
| C10 | 0.3910(16) | 0.1955(8) | 0 | H3 | 0.74856 | 0.63467 | 0.10834 |
| C11 | 0.559(2) | 0.3138(19) | 0.5 | H5 | 0.56509 | 0.56509 | 0.31657 |
| H1 | 0.25101 | -0.04094 | 0.5 | | | | |
| H3 | 0.3897(4) | 0.1062(2) | 0.6137(5) | | | | |
| H5 | 0.4291(6) | 0 | 0.8518(9) | | | | |
| Ow1 | 0.5568(9) | 0.4432(9) | 0.5 | | | | |
| Ow2 | 0.5 | 0.5 | 0.587(5) | | | | |
| Ow3 | 0.150(2) | 0 | 0 | | | | |
| Ow4 | 0.281(2) | 0.2150(16) | 0 | | | | |

FIG. 10

CRYSTALLINE HIGH DEGREE OF CONDENSATION TITANIUM-BASED INORGANIC-ORGANIC HYBRID SOLID MOF MATERIAL, METHOD FOR PREPARING SAME AND USES THEREOF

PRIORITY

This Application claims priority to European Patent Application n° EP 16305692.2 filed on 10 Jun. 2016, the entire contents of which are hereby incorporated by reference.

FIELD OF THE INVENTION

The present invention relates to a water-stable crystalline Titanium-based metal-organic framework (MOF) material having a high degree of condensation, i.e. an oxo to Ti ratio >1.0 in the case of pure Ti MOFs, or an oxo to metal ratio >1 for Ti-based MOFs doped with another metal than Ti; a process of preparing same and uses thereof, particularly for heterogeneously catalyzed chemical reactions, for gas storage/separation/purification, for information storage, laser printing or as an oxygen indicator, or as proton conductive material (fuel cells), optoelectronic material (photovoltaic cells including Grätzel cells), as a matrix for encapsulating active principles (medicaments, cosmetics), or else as sensing material.

BACKGROUND OF THE INVENTION

Metallo-organic lattices or metal-organic frameworks (MOFs) are porous coordination polymers, having an inorganic-organic hybrid framework that comprises metal ions and organic ligands coordinated to the metal ions. These materials are organized into one-, two- or three-dimensional lattices, in which the metallic species are joined together periodically by spacer ligands. The framework of these solids has both inorganic parts and organic parts, the cavities of which may be occupied by water molecules or by organic molecules that are easy to extract without deterioration of the backbone.

Another distinctive feature of certain hybrid solids is the existence of a flexibility of the lattice, greater than that encountered for purely inorganic phases. This is generally due to the use of flexible organic ligands (aliphatic chains), or to the shrinkage of the pores linked to the departure of molecules encapsulated within the pores.

These materials exhibit a crystalline structure, are usually porous and offer many potential industrial applications such as gas storage, adsorption of liquids, separation of liquids or gases, catalysis, controlled release of medicaments, etc.

Ti(IV) based metal-organic frameworks (MOFs) are of a high potential interest for both fundamental research and practical applications, with an aim to combine the excellent performances of $TiO_2$ in various applicable areas (catalysis, optoelectronics, cosmetics . . . ) with the permanent ordered porosity and/or possible ligand functionalization. However, the very high chemical reactivity of Ti(IV) species in polar solvents results in most cases in a poor control of the crystallization of Ti-based coordination compounds; thus, as a consequence, this dramatically limits the discovery and related developments of Ti-MOFs. Thus only very few examples of Ti-MOFs have been reported so far, including MIL-91, MIL-125, NTU-9, PCN-22, COK-69, Ti-CAT-5, MOF-901 and MIL-101(Ti). Among them, NTU-9, MOF-901 and Ti-CAT-5 possess either very narrow pores or a 2D structure which seriously limits their practical use. PCN-22 is made of very expensive porphyrinic linker and suffers from its unstability in the presence of water while the structure of COK-69 is very flexible and almost non porous under normal conditions. The Ti bisphosphonate MIL-91 and dicarboxylate MIL-125 are the only two really stable Ti-MOFs with 3D structures possessing accessible porosity for applications. Especially the amino group functionalized MIL-125 compound ($NH_2$-MIL-125) shows much better performance in stability, porosity and catalytic activity over all the other Ti-carboxylate MOFs. Thus it is considered as the benchmark material in the Ti-MOF field. Additionally when one compares the inorganic sub-building blocks in Ti-MOFs with $TiO_2$, the above reported Ti-MOFs are all built up from discrete Ti(IV) ions or Ti-oxo clusters or corner-sharing chains of metal octahedra, with a rather low Oxo to Ti ratio (1) which is much lower than for $TiO_2$ (Oxo/Ti=2). This ratio also known as the degree of condensation for Ti oxoclusters [1] is one of the driving force for their stability; usually the higher the rate the better the chemical stability of the resulting cluster. [2, 3] In addition, it is expected that higher condensation rates will lead to enhanced photo-physical or -catalytical properties.

Therefore, there remains a need for the development of Ti-based MOF materials having oxo/Ti ratio >1, with properties that outperform those of all the reported Ti-MOFs so far.

BRIEF DESCRIPTION OF THE DRAWINGS

FIG. 10 provides the crystal structure information of both LT and HT forms of Ti-based MOF solids according to the invention, obtained in Examples 1 and 2, respectively.

DEFINITIONS

Figure 1:
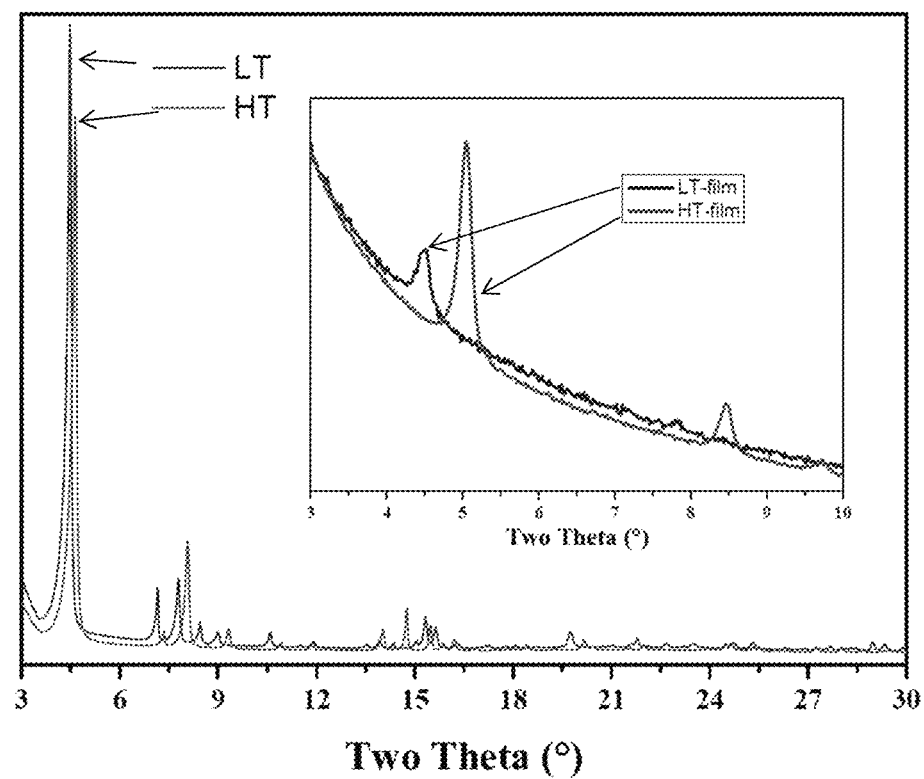
FIG. 1 shows powder X-ray diffraction (PXRD) ($\lambda_{Cu}$~1.5406 Å) patterns of both LT and HT forms of Ti-based MOF solids according to the invention, obtained in Examples 1 and 2, respectively.

To facilitate an understanding of the present invention, a number of terms and phrases are defined below:

As used herein other than the claims, the terms "a," "an," "the," and/or "said" means one or more. As used herein in the claim(s), when used in conjunction with the words "comprise," "comprises" and/or "comprising," the words "a," "an," "the," and/or "said" may mean one or more than one. As used herein and in the claims, the terms "having," "has," "is," "have," "including," "includes," and/or "include" has the same meaning as "comprising," "comprises," and "comprise." As used herein and in the claims "another" may mean at least a second or more. As used herein and in the claims, "about" refers to any inherent measurement error or a rounding of digits for a value (e.g., a measured value, calculated value such as a ratio), and thus the term "about" may be used with any value and/or range.

The phrase "a combination thereof" "a mixture thereof" and such like following a listing, the use of "and/or" as part of a listing, a listing in a table, the use of "etc." as part of a listing, the phrase "such as," and/or a listing within brackets with "e.g.," or i.e., refers to any combination (e.g., any sub-set) of a set of listed components, and combinations and/or mixtures of related species and/or embodiments described herein though not directly placed in such a listing are also contemplated. Such related and/or like genera(s), sub-genera(s), specie(s), and/or embodiment(s) described herein are contemplated both in the form of an individual component that may be claimed, as well as a mixture and/or a combination that may be described in the claims as "at least one selected from," "a mixture thereof" and/or "a combination thereof."

In general, the term "substituted" whether preceded by the term "optionally" or not, and substituents contained in formulae of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds.

As used herein, the term "alkyl", refers to straight and branched alkyl groups. In certain embodiments, as used herein, "lower alkyl" is used to indicate those alkyl groups (substituted, unsubstituted, branched or unbranched) having about 1-6 carbon atoms. Illustrative alkyl groups include, but are not limited to, for example, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, moieties and the like, which again, may bear one or more substituents.

As used herein, the term "aryl" refers to an aromatic system comprising at least one ring that satisfies Hückel's aromaticity rule. Said aryl is optionally substituted and may comprise from 6 to 50 carbon atoms, for example 6 to 20 carbon atoms, for example 6 to 10 carbon atoms. Examples of aryl groups include, but are not limited to, phenyl, indanyl, indenyl, naphthyl, phenanthryl and anthracyl.

In general, the term "heteroaryl moiety", as used herein, refers a cyclic unsaturated radical having from about five to about ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, triazolyl, oxazolyl, isooxazolyl, thiadiazolyl, oxadiazolyl, thiophenyl, furanyl, quinolinyl, isoquinolinyl, and the like.

The term "heteroalkyl", as used herein, refers to alkyl moieties in which one or more carbon atoms in the main chain have been substituted with a heteroatom. Thus, a heteroalkyl group refers to an alkyl chain which contains one or more oxygen, sulfur, nitrogen, phosphorus or silicon atoms, i.e., in place of carbon atoms, for example, at least one heteroatom to 20 heteroatoms, such as one to 15 heteroatoms, or one to 5 heteroatoms, or one, two, three or four heteroatoms. Heteroalkyl moieties may be branched or linear unbranched.

The term "Alkoxy", as used herein, refers to a moiety —O-alkyl, with exemplary embodiments including, but not limited to, methoxy, ethoxy, n-propoxy, isopropoxy, n-butoxy, t-butoxy, sec-butoxy, n-pentoxy, n-hexoxy.

The terms "halo" and "halogen" as used herein refer to an atom selected from fluorine, chlorine, bromine and iodine.

The abbreviation "acac", as used herein, refers to an acetylacetone ligand.

As used herein, the term "oxocluster" refers to a group of atoms containing at least two Ti metal atoms linked via ionocovalent bonds directly via O atoms.

As used herein, the term "independently" refers to the fact that the substituents, atoms or moieties to which these terms refer, are selected from the list of variables independently from each other (i.e., they may be identical or the same).

As used herein, the term "about" can refer to a variation of ±5%, ±10%, ±20%, or ±25%, of the value specified. For example, "about 50" percent can in some embodiments carry a variation from 45 to 55 percent. For integer ranges, the term "about" can include one or two integers greater than and/or less than a recited integer. Unless indicated otherwise herein, the term "about" is intended to include values, e.g., concentration values, proximate to the recited range that are equivalent in terms of the functionality of the individual ingredient, the composition, or the embodiment.

As used herein, the term "and/or" means any one of the items, any combination of the items, or all of the items with which this term is associated.

As will be understood by the skilled artisan, all numbers, including those expressing quantities of ingredients, properties such as cavity/pore size and BET specific surface area, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible subranges and combinations of subranges thereof, as well as the individual values making up the range, particularly integer values. A recited range includes each specific value, integer, decimal, or identity within the range.

Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, as used in an explicit negative limitation.

As used herein, the expression "three-dimensional structure" is understood to mean a three-dimensional sequence or repetition of units of any one of the oxocluster formulae defined in the present document (e.g., formula $(I_0)$, (I), or subvariants $(I^A)$ and $(I^B)$), as is conventionally understood in the field of MOF materials, which are also characterized as "organometallic polymers".

As used herein, the term "solid" refers to any type of crystalline material. Said solid may be, for example, in the form of crystals, powder or particles of varied forms, for example of spherical, lamellar, etc. form. The particles may be in the form of nanoparticles.

As used herein, the term "crystalline solid" or "crystalline material" refers to a solid material whose constituents (such as atoms, molecules, or ions) are arranged in a highly ordered microscopic structure, forming a crystal lattice that extends in all directions. Crystalline materials encompass monocrystalline and polycrystalline materials, and exclude amorphous materials. A monocrystalline MOF material (or a single crystal MOF) consists of a MOF in which the crystal lattice of the entire solid is continuous, unbroken (with no grain boundaries) to its edges. This is to be opposed to amorphous materials, in which the atomic order is limited to short range order only. Polycrystalline materials lie between these two extremes; they are made up of small crystals.

As used herein, the term "nanoparticle" refers to a particle smaller than 1 µm in size. In particular, the solid Ti-based MOF nanoparticles according to the invention may have a diameter of less than 1000 nanometers, preferably less than 500 nm, more preferably less than 250 nm and most particularly less than 100 nm.

As used herein, the term "ligand" refers to a ligand (including, for example, neutral species and ions) coordinated to at least two Ti metals (or two metals in the case of doped Ti-based materials according to a variant of the invention), which participates in providing distance between these metals and in forming empty spaces or pores.

DETAILED DESCRIPTION OF CERTAIN PREFERRED EMBODIMENTS OF THE INVENTION

In one aspect, the present invention provides crystalline titanium-based inorganic-organic hybrid metal-organic framework (MOF) material constituted of a three-dimensional succession of building units comprising an oxo-metal cluster; wherein the oxo-metal cluster atomic ratio O:metal is >1.0, preferably ≥1.1, most preferably ≥1.2; wherein at least 60%, preferably at least 65%, preferably at least 70%, of the MOF metal atoms are Ti atoms.

Crystalline titanium-based inorganic-organic hybrid MOF materials according to the invention may be constituted of a three-dimensional succession of building units of formula $I_0$:

$$M_aO_bL_xA_y \cdot n\text{Solv} \qquad (I_0)$$

wherein in each building unit,
  each occurrence of M independently represents Ti or another metal; such as Cu, Co, Ni, Mn, V, Cr, Fe, Ru, Sn, or Nb; wherein at least 60%, preferably at least 65%, preferably at least 70%, of M atoms in the MOF material are Ti atoms;
  each occurrence of L independently represents a bis-$C_6$aryl-containing tetracarboxylate ligand;
  each occurrence of A independently represents a ligand selected from $HCO_2^-$ or $MeCO_2^-$, preferably $HCO_2^-$; wherein a subset of A ligands in the MOF material may be replaced by ligands independently selected from $OH^-$, $H_2O$, $R_2$—$(SO_3)^-$, $R_2$—$(PO_3)H^-$, wherein $R^2$, for each occurrence, independently represents OH, $C_{1-12}$alkyl, $C_{1-12}$heteroalkyl, $C_{6-10}$aryl, $C_{5-10}$ heteroaryl; where each of the foregoing alkyl and heteroalkyl moiety may be linear or branched and cyclic or acyclic;
  a represents the number of M atoms in the building unit;
  b represents the number of O atoms in the building unit;
  x represents the number of L ligands in the building unit;
  y represents the number of A ligands in the building unit;
  n represents the average number of solvent molecules "Solv" coordinated to the metal centers M per building unit in the MOF material;
  and b>a.

Advantageously, the ratio b:a is ≥1.1, preferably ≥1.2, more preferably ≥1.3, most preferably ≥1.4.

Advantageously, all occurrences of A independently represent a ligand selected from $HCO_2^-$ or $MeCO_2^-$; preferably all occurrences of A represent $HCO_2^-$.

Crystalline titanium-based inorganic-organic hybrid MOF materials, as defined above, where at least a subset of building units (i.e., at least one building unit) of formula $I_0$, at least one occurrence of M is different than Ti, will be referred herein as "doped Ti-based MOF materials".

As such, the present invention provides the first crystalline titanium-based inorganic-organic hybrid solid metal organic framework (MOF) material having an oxo to Ti ratio >1.0, preferably ≥1.1, most preferably ≥1.2; wherein all the metal centers in the MOF material are Ti atoms (i.e. pure Ti-based MOF). Advantageously, the pure Ti-based MOF material may have an oxo to Ti ratio about 1.2, preferably about 1.3, preferably about 1.4, most preferably about 1.5. In other words, the present invention provides crystalline titanium-based inorganic-organic hybrid MOF material constituted of a three-dimensional succession of building units comprising an oxo-Ti cluster; wherein the oxo-Ti cluster atomic ratio O:Ti is >1.0, preferably ≥1.1, most preferably ≥1.2. Advantageously, the crystalline titanium-based inorganic-organic hybrid MOF material may be constituted of a three-dimensional succession of building units comprising an oxo-Ti cluster; wherein the oxo-Ti cluster atomic ratio O:Ti may be about 1.2, preferably about 1.3, preferably about 1.4, most preferably about 1.5.

As mentioned above and detailed infra, Ti-based MOF materials according to the invention may be doped with one or more metals, such as Cu, Co, Ni, Mn, V, Cr, Fe, Ru, Sn, or Nb. As such, the present invention also provides crystalline doped titanium-based inorganic-organic hybrid solid metal organic framework (MOF) material constituted of a three-dimensional succession of building units comprising an oxo to metal ratio O:M>1.0, preferably ≥1.1, most preferably ≥1.2; wherein the oxo to metal ratio is calculated based on the total number of metal atoms in the MOF material (i.e., Ti atoms+other metal atoms that replace Ti atoms in the MOF material lattice). Advantageously, the doped Ti-based MOF material may have an oxo to metal ratio O:M about 1.2, preferably about 1.3, preferably about 1.4, most preferably about 1.5. Advantageously, the Ti atoms in the MOF materials represent at least 60%, preferably at least 65%, preferably at least 70%, of the total metal atoms present in the doped MOF lattice. In other words, the present invention provides crystalline titanium-based inorganic-organic hybrid MOF material constituted of a three-dimensional succession of building units comprising an oxo-metal cluster; wherein the oxo-metal cluster atomic ratio O:metal is >1.0, preferably ≥1.1, most preferably ≥1.2; wherein Ti atoms preferably represent at least 60%, preferably at least 65%, preferably at least 70%, of the total metal atoms present in the doped MOF lattice. Advantageously, the crystalline titanium-based inorganic-organic hybrid MOF material may be constituted of a three-dimensional succession of building units comprising an oxo-metal cluster; wherein the oxo-metal cluster atomic ratio O:M may be about 1.2, preferably about 1.3, preferably about 1.4, most preferably about 1.5; wherein Ti atoms preferably represent at least 60%, preferably at least 65%, preferably at least 70%, of the total metal atoms present in the doped MOF lattice.

Advantageously, in the doped crystalline Ti-based MOF materials according to the invention, the Ti atoms preferably represent at least 65%, preferably at least 70%, preferably at least 71%, preferably at least 72%, preferably at least 73%, preferably at least 74%, preferably at least 75%, preferably at least 76%, preferably at least 77%, preferably at least 78%, preferably at least 79%, preferably at least 80%, preferably at least 81%, preferably at least 82%, preferably at least 83%, preferably at least 84%, preferably at least 85%, preferably at least 86%, preferably at least 87%, preferably at least 88%, preferably at least 89%, preferably at least 90%, preferably at least 91%, preferably at least 92%, preferably at least 93%, preferably at least 94%, preferably at least 95%, preferably at least 96%, preferably at least 97%, preferably at least 98%, preferably at least 99%.

Advantageously, in the pure and/or doped crystalline Ti-based MOF materials according to the invention, the metal atoms (Ti atoms, in case of pure crystalline Ti-based MOF materials) may be coordinated to at least one bis-$C_6$aryl-containing tetracarboxylate ligand. As used herein, the term "bis-$C_6$aryl-containing tetracarboxylate ligand" refers to a ligand containing exactly two non-fused $C_6$aryl groups and four carboxylate groups. The two non-fused $C_6$aryl groups may be bound to each other via a covalent bond, or may be separated by a one- or two-atom long chain. The bis-$C_6$aryl-containing tetracarboxylate ligand may be optionally substituted with substituents other than $CO_2H$, carboxylate or salt thereof, and $C_6$aryl groups. For example, the bis-$C_6$aryl-containing tetracarboxylate ligand may be substituted with one or more substituents independently selected from halogen atom, OH, $NH_2$, $NO_2$ or $C_{1-6}$alkyl. Advantageously, the at least one bis-$C_6$aryl-containing tetracarboxylate ligand may have the structure of formula (II):

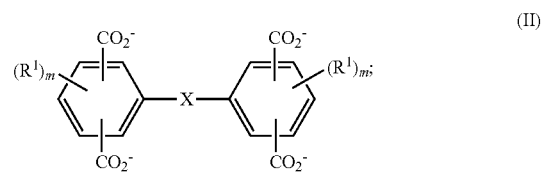

wherein X represents a covalent bond, C=O, $CH_2$, N=N, NH, O, S, $SO_2$, C=C, —O—$(CH_2)_p$—O—, —NH—$(CH_2)_p$—NH— or —S—$(CH_2)_p$—S— where p represents an integer ranging from 1 to 4; preferably C=O, $CH_2$, N=N, NH, O, S, $SO_2$, —O—$(CH_2)_p$—O—, —NH—$(CH_2)_p$—NH— or —S—$(CH_2)_p$—S—; most preferably C=O, $CH_2$, or N=N; and each occurrence of m independently represents an integer from 1 to 3; and each occurrence of $R^1$ independently represents H, a halogen atom, OH, $NH_2$, $NO_2$ or a $C_{1-6}$alkyl, preferably each occurrence of $R^1$ represents H.

When X is N=N or C=C, the at least one bis-$C_6$aryl-containing tetracarboxylate ligand of formula (II) may be of conformation cis or trans, preferably trans.

Among the bis-$C_6$aryl-containing tetracarboxylate ligand defined herein, mention may be made of ligands of any one of the following formulae $(II_1)$ through $(II_{16})$:

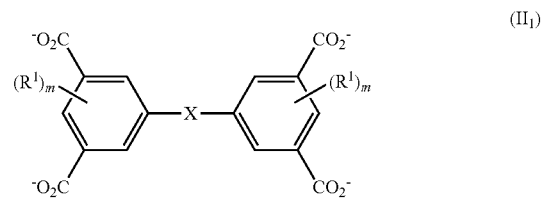

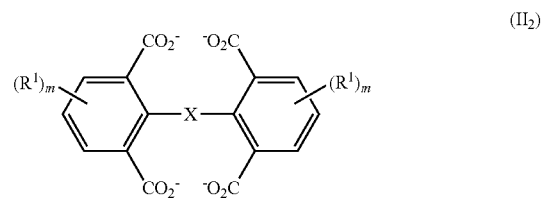

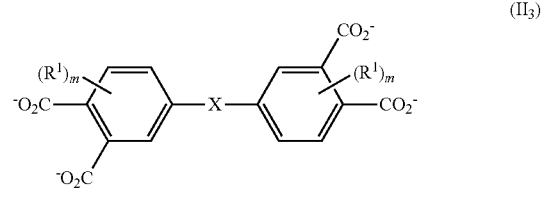

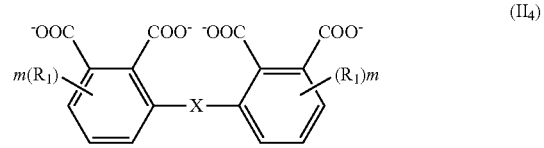

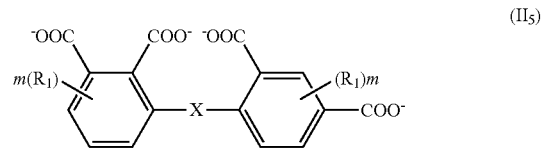

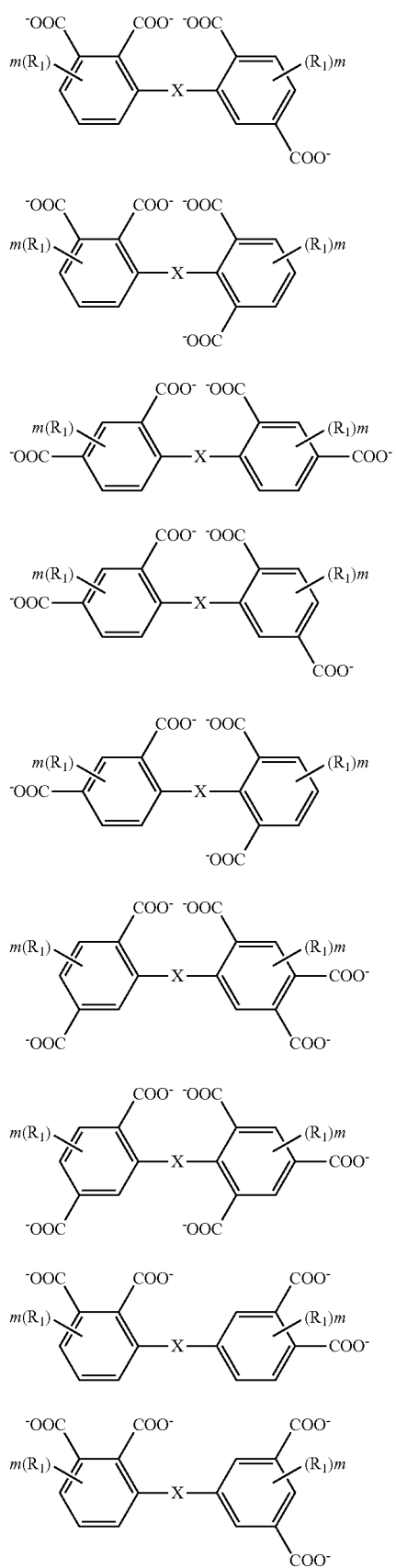

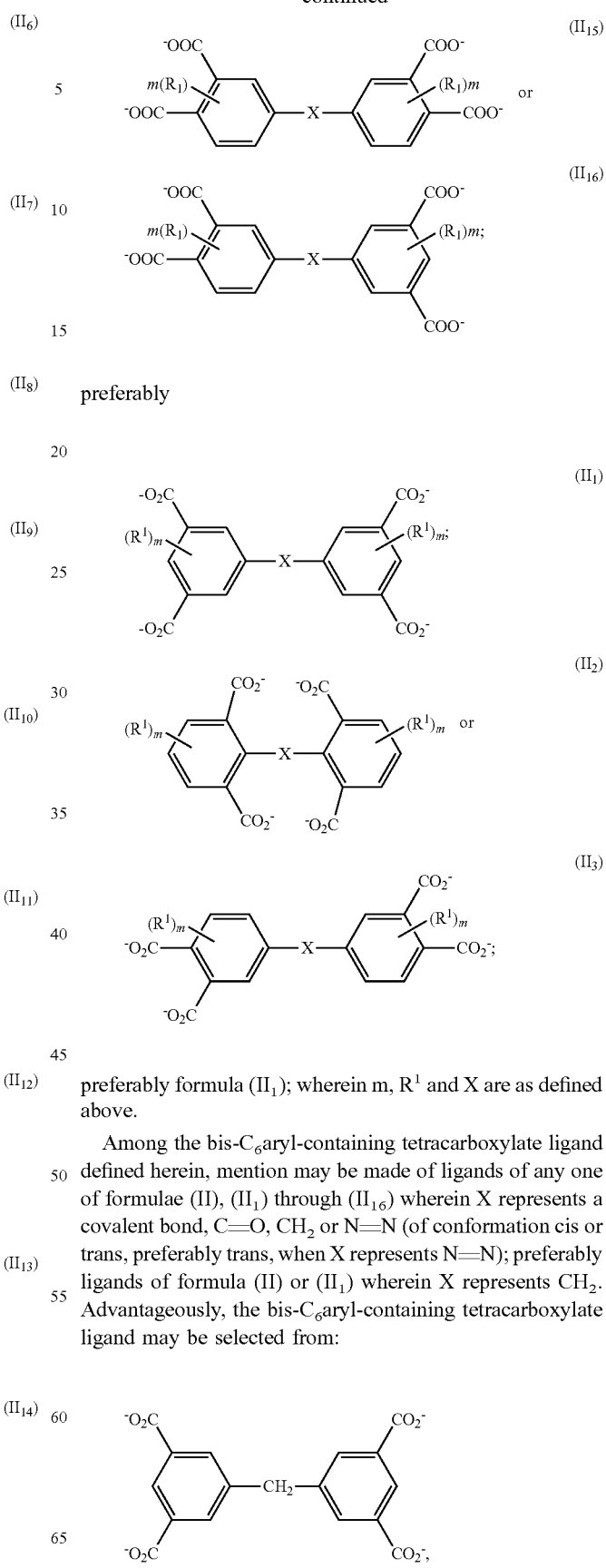

preferably formula (II₁); wherein m, R¹ and X are as defined above.

Among the bis-C₆aryl-containing tetracarboxylate ligand defined herein, mention may be made of ligands of any one of formulae (II), (II₁) through (II₁₆) wherein X represents a covalent bond, C=O, CH₂ or N=N (of conformation cis or trans, preferably trans, when X represents N=N); preferably ligands of formula (II) or (II₁) wherein X represents CH₂. Advantageously, the bis-C₆aryl-containing tetracarboxylate ligand may be selected from:

-continued

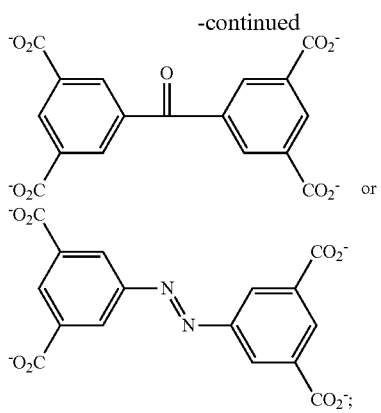

preferably

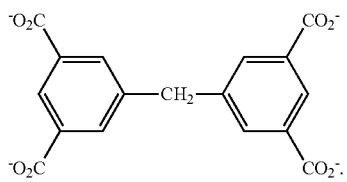

According to the invention, in the pure and/or doped crystalline Ti-based MOF materials according to the invention, the Ti-oxo or metal-oxo clusters may comprise any conventional ligand known in the art of MOFs, in addition to the at least one bis-$C_6$aryl-containing tetracarboxylate ligand. For example, the Ti-oxo or metal-oxo clusters of the pure and/or doped crystalline Ti-based MOF materials according to the invention, may comprise ligands independently selected from $HCO_2^-$, $MeCO_2^-$, $OH^-$, $H_2O$, $R^2$—$(SO_3)^-$, $R^2$—$(PO_3)H^-$, wherein $R^2$, for each occurrence, independently represents OH, $C_{1-12}$alkyl, $C_{1-12}$heteroalkyl, $C_{6-10}$aryl, $C_{5-10}$ heteroaryl; where each of the foregoing alkyl and heteroalkyl moiety may be linear or branched and cyclic or acyclic. One or more solvent and/or water molecules may additionally be coordinated to the Ti center (or metal center in the case of doped Ti-based MOFs according to the invention) in each Ti-oxo cluster (or in each metal-oxo cluster in the case of doped Ti-based MOFs according to the invention).

The solvent molecules "Solv" in Formula ($I_0$) may be any solvent that can participate in coordination with the MOF metal ions and/or that can act as a guest molecule in the final MOF lattice structure. It may be any one or more of the solvents used in the MOF assembly process, preferably polar solvents. Conventional solvents used in MOF synthesis include $H_2O$, dimethylacetamide (DMA), diethylacetamide (DEA), dipropylacetamide (DPA), diethylpropanamide (DEP), dipropylpropanamide (DPP), dimethyl sulfoxide (DMSO), dimethylformamide (DMF), diethylformamide (DEF), etc. Additional solvents are described on page 33 of this document. In formula ($I_0$), the occurrences of Solv may be the same or different. For example, when the MOF is made by a process using a mixed solvent system (e.g., $H_2O$ and DMF), occurrences of Solv may be different. For example, Solv may represent $H_2O$ molecules.

As used herein, the term "titanium-based inorganic-organic hybrid solid material" is interchangeable with "crystalline titanium-based inorganic-organic hybrid MOF material", and refers to both pure and doped crystalline Ti-based MOF materials.

As used herein, the term "crystalline pure Ti-based MOF material" refers to a crystalline Ti-based MOF material wherein all the metal centers in the MOF materials are Ti atoms.

As used herein, the term "crystalline doped Ti-based MOF material" refers to a crystalline pure Ti-based MOF material, as defined above, wherein some of the Ti atoms are replaced with one or more metal atoms different from Ti. In other words, the metal atoms different from Ti do not occupy distinct crystallographic positions from the original Ti sites. For example, the other metal atoms may be selected from Cu, Co, Ni, Mn, V, Cr, Fe, Ru, Sn, or Nb. It is understood that in crystalline doped Ti-based MOF material according to the present invention, the Ti atoms in the doped material's lattice are preponderant as compared to the other metal atoms different from Ti. For example, the Ti metal sites may represent at least 60%, preferably at least 65%, preferably at least 70%, preferably at least 71%, preferably at least 72%, preferably at least 73%, preferably at least 74%, preferably at least 75%, preferably at least 76%, preferably at least 77%, preferably at least 78%, preferably at least 79%, preferably at least 80%, preferably at least 81%, preferably at least 82%, preferably at least 83%, preferably at least 84%, preferably at least 85%, preferably at least 86%, preferably at least 87%, preferably at least 88%, preferably at least 89%, preferably at least 90%, preferably at least 91%, preferably at least 92%, preferably at least 93%, preferably at least 94%, preferably at least 95%, preferably at least 96%, preferably at least 97%, preferably at least 98%, preferably at least 99% of the total metal atoms present in the doped MOF lattice.

In certain embodiments, crystalline titanium-based inorganic-organic hybrid MOF materials based on oxo clusters $Ti_8O_{10}$ are excluded, particularly those $Ti_8O_{10}$ cluster MOFs containing a bis-phenyl-containing tetracarboxylate ligand having the structure:

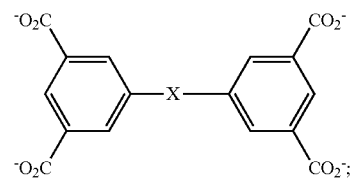

wherein X represents N=N, C=C, —(CH$_2$)$_2$— or —C≡C—.

Advantageously, the titanium-based inorganic-organic hybrid solid material may be constituted exclusively of a three-dimensional succession of building units of formula (I) below:

$$Ti_{12}O_xL_3A_y \qquad (I)$$

wherein each occurrence of L independently represents a bis-$C_6$aryl-containing tetracarboxylate ligand having the structure of formula (II):

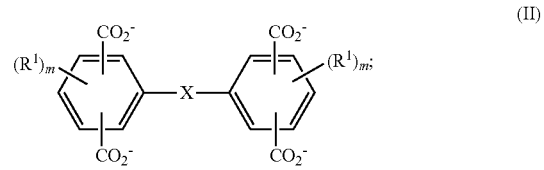

wherein X represents a covalent bond, C=O, CH$_2$, N=N, NH, O, S, SO$_2$, C=C, —O—(CH$_2$)$_p$—O—, —NH—(CH$_2$)$_p$—NH— or S—(CH$_2$)$_p$—S— where p represents an integer ranging from 1 to 4; preferably C=O, CH$_2$, N=N, NH, O, S, SO$_2$, —O—(CH$_2$)$_p$—O—, —NH—(CH$_2$)$_p$—NH— or S—(CH$_2$)$_p$—S—; most preferably C=O, CH$_2$, or N=N; (of conformation cis or trans, preferably trans, when X represents C=C or N=N)

each occurrence of m independently represents an integer from 1 to 3; and each occurrence of R$^1$ independently represents H, a halogen atom, OH, NH$_2$, NO$_2$ or a C$_{1-6}$alkyl, preferably each occurrence of R$^1$ represents H;

each occurrence of A independently represents a ligand selected from HCO$_2^-$, MeCO$_2^-$, OH$^-$, H$_2$O, R$^2$—(SO$_3$)$^-$, R$^2$—(PO$_3$)H$^-$, wherein R$^2$, for each occurrence, independently represents OH, C$_{1-12}$alkyl, C$_{1-12}$heteroalkyl, C$_{6-10}$aryl, C$_{5-10}$heteroaryl; where each of the foregoing alkyl and heteroalkyl moiety may be linear or branched and cyclic or acyclic;

x represents 15 or 18;

y represents 0 or 6;

the titanium atoms form a purely inorganic elementary building block constituted of titanium oxo complexes; wherein the units of formula (I) together form a three-dimensional structure that crystallizes in the hexagonal crystal system; in case of encapsulation of guests molecules into the pores and/or through functionalization of the framework it might happen that the structure, while retaining the initial topology, exhibits a lower symmetry (orthorhombic, monoclinic or triclinic) particularly); and wherein the building unit optionally further comprises solvent molecules coordinated to titanium metal centers of the building units.

The solid material in accordance with the invention, also referred to herein as pure or doped titanium-based MOF, has the advantage of being based on titanium and of having a controlled and highly organized crystalline structure, with a particular topology, a particular distribution and an oxo/Ti ratio >1.0 (or oxo/metal ratio >1.0 in case of doped Ti-based MOFs according to the invention), that gives this material useful specific properties.

The crystalline spatial organization of the solid material of the present invention, together with usually high degree of condensation, is the basis of the particular characteristics and properties of this material, and for example governs the size of the cavities (or pores) which has an influence on the specific surface area of the material and on the capacities for storing gases or for adsorbing liquids for example.

In the units of formula (I), (I$^A$) or (I$^B$), among the bis-C$_6$aryl-containing tetracarboxylate ligand defined for L, mention may be made of ligands of any one of formulae (II$_1$) through (II$_{16}$) as defined above; preferably any one of formulae (II$_1$), (II$_2$) or (II$_3$):

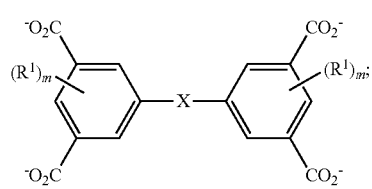

(II$_1$)

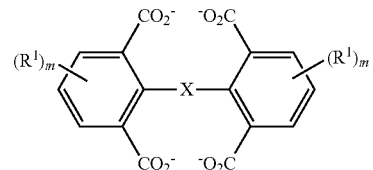

(II$_2$)

or

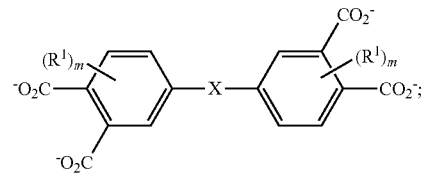

(II$_3$)

preferably formula (II$_1$).

In the units of formula (I), (I$^A$) or (I$^B$), among the bis-C$_6$aryl-containing tetracarboxylate ligand defined for L, mention may be made of ligands of any one of formulae (II), (II$_1$) through (II$_{16}$) as defined above; preferably ligands of any one of formulae (II), (II$_1$), (II$_2$) or (II$_3$); wherein X represents a covalent bond, C=O, CH$_2$ or N=N (of conformation cis or trans, preferably trans, when X represents N=N); most preferably ligands of formula (II) or (II$_1$) wherein X represents CH$_2$.

Advantageously, in the units of formula (I$_0$), (I), (I$^A$) or (I$^B$), each occurrence of L may represent:

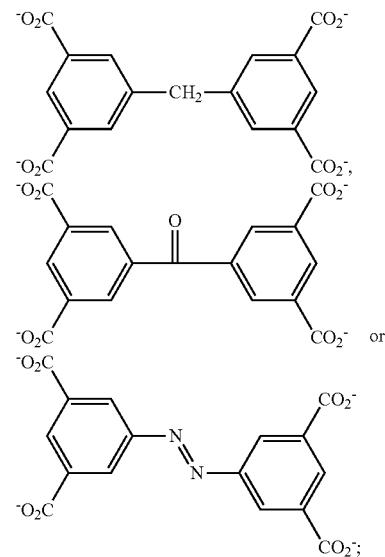

or preferably

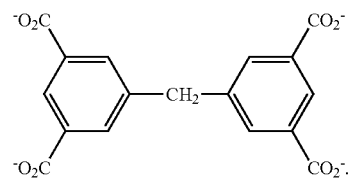

In the units of formula (I$_0$), (I), (I$^A$) or (I$^B$), among the ligands defined for A, mention may be made of the formate ligand HCO$_2^-$ or the acetate ligand MeCO$_2^-$; preferably the formate ligand HCO$_2^-$. As such, in a variant, in the material constituted of building units of formula (I$_0$), (I), (I$^A$) or (I$^B$), wherein L may be any variant described above, each occurrence of A may represent a formate ligand HCO$_2^-$ or an acetate ligand MeCO$_2^-$; preferably each occurrence of A may represent a formate ligand HCO$_2^-$. In another variant, occurrences of A as formate or acetate ligand may be replaced by another ligand selected from OH$^-$, H$_2$O, R$^2$—(SO$_3$)$^-$, R$^2$—(PO$_3$)H$^-$, wherein R$^2$, for each occurrence, independently represents OH, C$_{1-12}$alkyl, C$_{1-12}$heteroalkyl, C$_{6-10}$aryl, C$_{5-10}$ heteroaryl; where each of the foregoing alkyl and heteroalkyl moiety may be linear or branched and cyclic or acyclic.

For example, in the material constituted of building units of formula (I$_0$), (I), (I$^A$) or (I$^B$), occurrences of A as formate or acetate ligand may be replaced by another ligand selected from OH$^-$, H$_2$O, sulfanilate, pyridinyl-3-sulfonate, (1R)-(−)-camphor-10-sulfonate, hydroxylamine-O-sulfonate, 3-aminopropyl-1-sulfonate, 4-hydrozinobenzenesulfonate, 5-sulfosalicylate, or isoquinolinyl-5-sulfonate.

Advantageously, in formula (I), when y is 0 or 6 and A represents a formate ligand HCO$_2^-$, the crystal topology shall be preferably related to an hexagonal crystal system and the P6/mmm space group or a sub-group or a multiple unit cell.

Advantageously, the three-dimensional structure of building units of formula (I) defines cavities having a free diameter between 3 and 14 Å that are accessible through apertures having dimensions of 3 to 14 Å.

In certain embodiments, the three-dimensional structure of building units of formula (I) defines cavities having a free diameter between 10 to 12 Å. This may be the case for example for Ti-based MOF materials of the invention where the building units of the material have the formula Ti$_{12}$O$_{15}$L$_3$A$_6$.nH$_2$O (I$^A$) where A represents formate or acetate ligands.

In certain embodiments, the three-dimensional structure of building units of formula (I) defines cavities having a free diameter between 10 to 14 Å. This may be the case for example for Ti-based MOF materials of the invention where the building units of the material have the formula Ti$_{12}$O$_{15}$L$_3$A$_6$.nH$_2$O (I$^A$) where A represents a ligand other than formate or acetate (i.e., in functionalized Ti-based MOFs).

In certain embodiments, the three-dimensional structure of building units of formula (I) defines cavities having a free diameter between 3 to 8 Å. This may be the case for example for Ti-based MOF materials of the invention where the building units of the material have the formula Ti$_{12}$O$_{18}$L$_3$ (I$^B$).

Advantageously, the three-dimensional structure of building units of formula (I) defines at least two different sized and shaped tunnels.

For example, Ti-based MOF materials of the invention where the building units of the material have the formula Ti$_{12}$O$_{18}$L$_3$ (I$^B$) may exhibit hexagonal shaped tunnels the diameter of which may be up to 8 Å, and rectangular shaped tunnels of dimension 2 Å*5 Å.

In another example, Ti-based MOF materials of the invention where the building units of the material have the formula Ti$_{12}$O$_{15}$L$_3$A$_6$.nH$_2$O (I$^A$) may exhibit hexagonal shaped tunnels the diameter of which may be up to 14 Å, and rectangular shaped tunnels of dimension 1.3 Å*3 Å.

In one variant, the building units of the material may have the formula (I$^A$):

$$Ti_{12}O_{15}L_3A_6 \cdot nH_2O \quad (I^A)$$

wherein A and L are as defined in any variant described above, and n represents the average number of water molecules that are coordinated to the titanium metal centers per building unit in the material.

In another variant, the building units of the material may have the formula (I$^B$):

$$Ti_{12}O_{18}L_3 \quad (I^B)$$

wherein L is as defined in any variant described above.

Advantageously, the material constituted of building units of formula (I$_0$) or (I), including formulae (I$^A$) and (I$^B$), may have a BET specific surface area ranging from 100 to 2000 m$^2$/g; preferably from 100 to 1000 m$^2$/g; most preferably from 100 to 800 m$^2$/g.

Advantageously, the material constituted of building units of formula (I$_0$) or (I), including formulae (I$^A$) and (I$^B$), may have a pore volume of 0.1 to 1.5, preferably from 0.3 to 0.8 cm$^3$/g. As used herein, the pore volume refers to the volume of gas accessible for the gas and/or liquid molecules and corresponds to the volume inside what are referred to either as "cavities", "cages" or "pores" in the text of the present application.

Advantageously, the crystalline titanium-based MOFs according to the invention, including titanium-based MOF material constituted of building units of formula (I$_0$) or (I), including formulae (I$^A$) and (I$^B$), may be doped with one or more metals, such as Cu, Co, Ni, Mn, V, Cr, Fe, Ru, Sn, or Nb.

As used herein, with respect to doping with one or more metals, the term "doping" or "doped" refers to placing other metal atoms such as Cu, Co, Ni, Mn, V, Cr, Fe, Ru, Sn, or Nb, in the titanium-based material lattice in place of titanium atoms. For example a "Cu-doped material" is a titanium-based material according to the invention that has "implanted" Cu atoms replacing titanium atoms in the material's lattice.

As such, metal ions such as Cu$^{2+}$, Fe$^{2+}$, Fe$^{3+}$, Co$^{2+}$, Co$^{3+}$, Ni$^{2+}$, Mn$^{2+}$, Mn$^{3+}$, Mn$^{4+}$, V$^{3+}$, V$^{4+}$, Cr$^{3+}$, Ru$^{3+}$, Ru$^{4+}$, Sn$^{4+}$, Nb$^{4+}$+ or Nb$^{5+}$, may be incorporated into the material's structure in place of Titanium metal centers.

Due to their structural features and high condensation degree, the Ti-based MOF material according to the present invention may be used as a catalyst support for carrying out heterogeneously catalyzed chemical reactions, or as a gas storage/separation/purification material, or as a matrix for encapsulating active principles (medicaments, cosmetics), or as a photochromic material for information storage, laser printing or as an oxygen indicator, or as proton conductive material (fuel cells), or a optoelectronic material (photovoltaic cells including Grätzel cells), or else as sensing material.

The reader may refer to the indicated literature references for guidance as to how the Ti-based MOFs of the invention may be used in the various applications of interest:

Heterogeneous catalysis, particularly photocatalysis [4]
Gas storage [5]
Separation of fluids [6]
Fuel-cells (proton conductive materials) [7]
Optoelectronics (Photovoltaics . . . ) [8]
Sensing [9]
Biomedicine, health-care, cosmetics [10]

As non-limiting examples, the solid Ti-based MOF material in accordance with the present invention more particularly being used:

for the adsorption of greenhouse gases ($CO_2$, $CH_4$), in the presence of various contaminants (water, $N_2$, CO, $H_2S$, etc.) in processes for capturing flue gases from factories (steelworks, cement works, thermal power plants, etc.), from units for producing methane or hydrogen from the combustion of biomass or the gasification of coal, The low production cost of these materials, combined with their non-toxicity and their good stability (thermal stability, moisture resistance or resistance to dihydrogen sulfide) makes them the candidates of choice for large-scale applications of this type;

for the separation of fluids (gases, vapors, liquids) such as the separation of aromatic compounds (isomers of xylene), of branched alkanes (octane number), of biomass derivatives (phenols . . . ), the purification of fuels, etc.;

in biology/medicine/cosmetics, for the adsorption or encapsulation of active (pharmaceutical or cosmetic) principles of interest for the purpose either of releasing them in a controlled manner in order to provide doses at an effective level therapeutically for a suitable period, or of protecting them with respect to the outside environment (from moisture for example). As such, titanium is a metal that is not very toxic (lethal dose ($LD_{50}$) greater than 5 g/kg) in the same way as carboxylic acids in general, which gives these solids (Titanium-based MOFs with high condensation degree) an a priori low toxicity that is very advantageous for this type of application. Its very high chemical stability might particularly be of interest to prevent from a fast release of the cargos. The UV adsorption properties of titanium may be applied to the field of UV-screening substances used in cosmetics, in particular with a suitable choice of organic spacer that itself also adsorbs in this wavelength range. The solid Ti-based MOF materials in accordance with the invention may also be used for the removal of toxins, for detoxification (for eliminating a posteriori toxins in the body), or for purifying biological fluids (urine, blood, etc.).

The solid Ti-based MOF material in accordance with the invention may be prepared under solvothermal or reflux conditions.

Thus, in another aspect, there is provided a process for preparing crystalline pure titanium-based inorganic-organic hybrid solid material having an oxo to Ti ratio >1.0, preferably ≥1.1, most preferably ≥1.2; said process comprising at least one reaction step (i) of reacting in a suitable solvent system:

at least one titanium precursor selected from $TiCl_4$, TiO(acac)$_2$, $TiOSO_4$ (titanyl sulfate), $Ti(SO_4)_2$ or titanium alkoxides of formula (III):

$$Ti(OR^3)_4 \quad (III)$$

wherein each occurrence of $R^3$ independently represents a linear or branched $C_{1-6}$alkyl moiety;

formic acid or acetic acid or acetic anydride, preferably formic acid; and a bis-$C_6$aryl-containing tetradentate ligand precursor having four —C(=O)R$_4$ moieties: wherein each occurrence of $R^4$ independently represents —OH, —OM$_0$ where M$_0$ represents an akali metal cation, a halogen atom, or a —OR$^5$, —O—C(=O)R$^5$ or —NR$^5$R$^{5'}$ moiety, wherein R$^5$ and R$^{5'}$ independently represent $C_{1-12}$alkyl; preferably each occurrence R$^4$ represents OH.

This leads to the formation of a crystalline pure Ti-based material where the Ti atoms form a three dimensional array of Ti-oxo clusters linked with bis-$C_6$aryl-containing tetracarboxylate ligands, where the Ti atoms are further coordinated to formate or acetate ligands, preferably formate ligands; and optionally to solvent molecules such as water molecules.

The bis-$C_6$aryl-containing tetradentate ligand precursor may have the following structure:

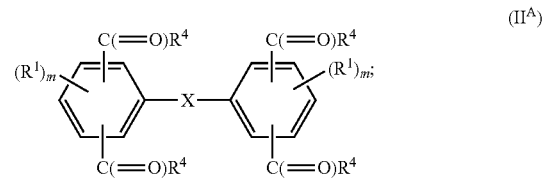

(II$^A$)

wherein X represents a covalent bond, C=O, $CH_2$, N=N, NH, O, S, $SO_2$, C=C, —O—$(CH_2)_p$—O—, —NH—$(CH_2)_p$—NH— or S—$(CH_2)_p$—S— where p represents an integer ranging from 1 to 4; preferably C=O, $CH_2$, N=N, NH, O, S, $SO_2$, —O—$(CH_2)_p$—O—, —NH—$(CH_2)_p$—NH— or S—$(CH_2)_p$—S—; most preferably C=O, $CH_2$, or N=N;

each occurrence of m independently represents an integer from 1 to 3; and each occurrence of $R^1$ independently represents H, a halogen atom, OH, $NH_2$, $NO_2$ or a $C_{1-6}$alkyl, preferably each occurrence of $R^1$ represents H; and each occurrence of $R^4$ independently represents —OH, —OM$_0$ where M$_0$ represents an akali metal cation, a halogen atom, or a —OR$^5$, —O—C(=O)R$^5$ or NR$^5$R$^{5'}$ moiety, wherein R$^5$ and R$^{5'}$ independently represent $C_{1-12}$alkyl; preferably each occurrence of $R^1$ represents H and each occurrence of $R^4$ represents OH; most preferably X represents $CH_2$ and each occurrence of $R^1$ represents H and each occurrence of $R^4$ represents OH.

Accordingly, the resulting crystalline pure Ti-based material will comprise bis-$C_6$aryl-containing tetracarboxylate ligands having the structure:

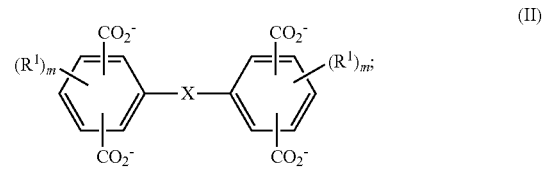

(II)

wherein X, m and $R^1$ are as defined above; preferably each occurrence of $R^1$ represents H; most preferably X represents $CH_2$ and each occurrence of $R^1$ represents H.

Advantageously, the process may comprise a further step of isolating the resulting titanium-based inorganic-organic hybrid solid material obtained from step (i), and reacting it with HCl, $H_2SO_4$, $H_3PO_4$, $R^2$—$SO_3H$, or $R^2$—$PO_3H_2$, wherein $R^2$, for each occurrence, independently represent OH, $C_{1-12}$alkyl, $C_{1-12}$heteroalkyl, $C_{6-10}$aryl, $C_{5-10}$heteroaryl; where each of the foregoing alkyl and heteroalkyl moiety may be linear or branched and cyclic or acyclic. This step advantageously leads to the exchange of formate/acetate ligands with OH/$H_2O$ ligands. It may alternatively be effected by thermal treatment, as described infra.

In another aspect, there is provided a process for preparing crystalline titanium-based inorganic-organic hybrid solid material constituted exclusively of a three-dimensional succession of building units of formula (I) as defined generally above and in any variant herein, said process comprising at least one reaction step (i) of reacting in a suitable solvent system:
at least one titanium precursor selected from TiCl$_4$, TiO(acac)$_2$, TiOSO$_4$ (titanyl sulfate), Ti(SO$_4$)$_2$ or titanium alkoxides of formula (III):

Ti(OR$^3$)$_4$  (III)

wherein each occurrence of R$^3$ independently represents a linear or branched C$_{1-6}$alkyl moiety;
formic acid or acetic acid or acetic anydride, preferably formic acid; and
a bis-C$_6$aryl-containing tetradentate ligand precursor having the structure (II$^A$):

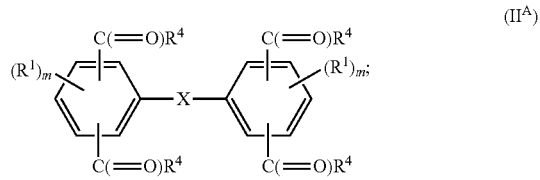

(II$^A$)

wherein X represents a covalent bond, C=O, CH$_2$, N=N, NH, O, S, SO$_2$, C=C, —O—(CH$_2$)$_p$—O—, —NH—(CH$_2$)$_p$—NH— or S—(CH$_2$)$_p$—S— where p represents an integer ranging from 1 to 4; preferably C=O, CH$_2$, N=N, NH, O, S, SO$_2$, —O—(CH$_2$)$_p$—O—, —NH—(CH$_2$)$_p$—NH— or S—(CH$_2$)$_p$—S—; most preferably C=O, CH$_2$, or N=N;
each occurrence of m independently represents an integer from 1 to 3; and each occurrence of R$^1$ independently represents H, a halogen atom, OH, NH$_2$, NO$_2$ or a C$_{1-6}$alkyl, preferably each occurrence of R$^1$ represents H; and
each occurrence of R$^4$ independently represents —OH, —OM$_0$ where M$_0$ represents an akali metal cation, a halogen atom, or a —OR$^5$, —O—C(=O)R$^5$ or NR$^5$R$^{5'}$ moiety, wherein R$^5$ and R$^{5'}$ independently represent C$_{1-12}$ alkyl; preferably each occurrence of R$^1$ represents H and each occurrence of R$^4$ represents OH; most preferably X represents CH$_2$ and each occurrence of R$^1$ represents H and each occurrence of R$^4$ represents OH;
under suitable conditions to form a titanium-based inorganic-organic hybrid solid material composed of a three-dimensional succession of building units of formula (I$^4$):

Ti$_{12}$O$_{15}$L$_3$A$_6$·nH$_2$O  (I$^4$)

wherein A represents a formate ligand HCO$_2^-$ or an acetate ligand MeCO$_2^-$; preferably A represents a formate ligand HCO$_2^-$; n represents the average number of water molecules that are coordinated to the titanium metal centers per building unit in the material; and L represents a bis-C$_6$aryl-containing tetracarboxylate ligand having the structure (II):

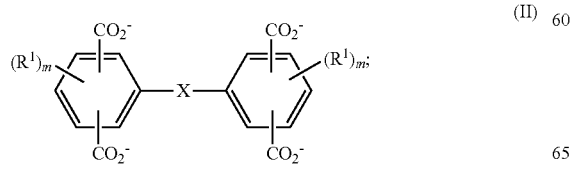

(II)

wherein X, m and R$^1$ are as defined above; preferably each occurrence of R$^1$ represents H; most preferably X represents CH$_2$ and each occurrence of R$^1$ represents H.

For any variant of the process described herein, among the bis-C$_6$aryl-containing tetradentate ligand precursors, mention may be made of ligand precursors of any one of the following formulae (II$^4_1$) through (II$^4_{16}$):

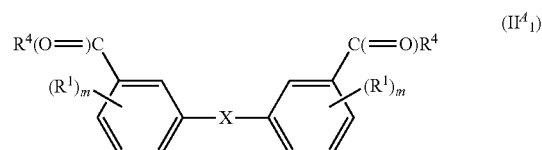

(II$^4_1$)

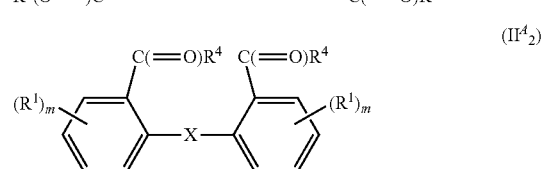

(II$^4_2$)

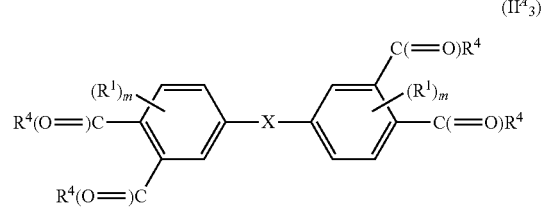

(II$^4_3$)

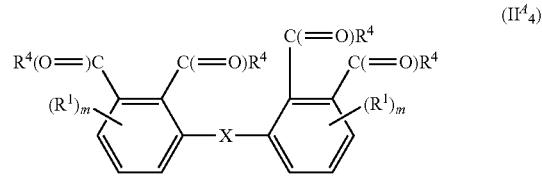

(II$^4_4$)

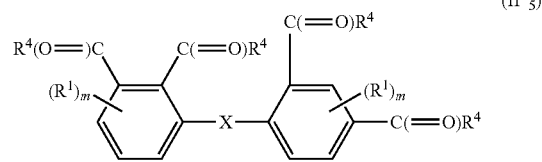

(II$^4_5$)

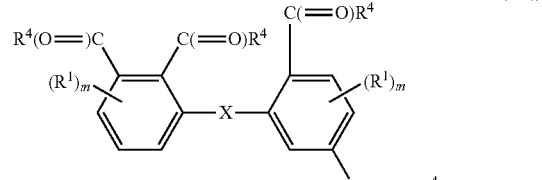

(II$^4_6$)

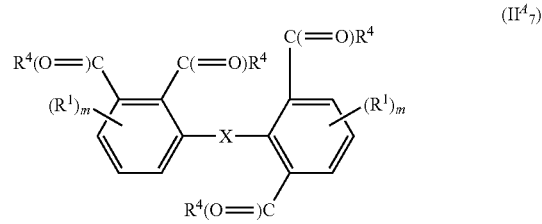

(II$^4_7$)

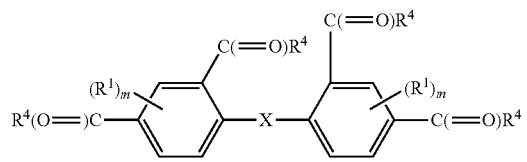
(II⁴₈)

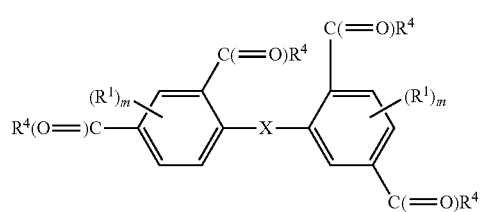
(II⁴₉)

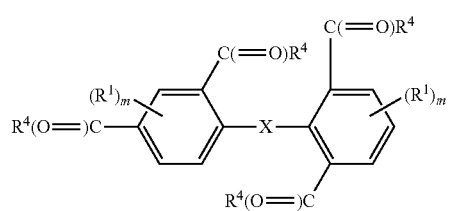
(II⁴₁₀)

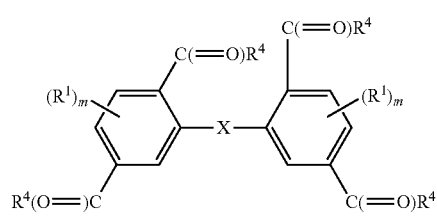
(II⁴₁₁)

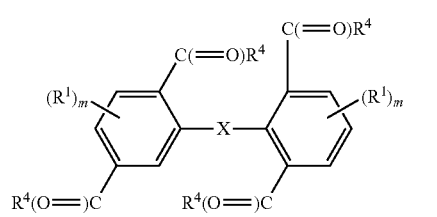
(II⁴₁₂)

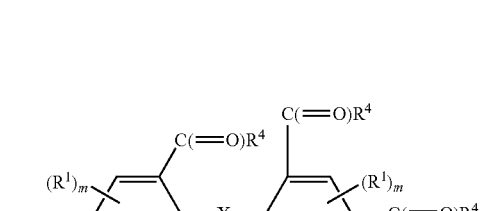
(II⁴₁₃)

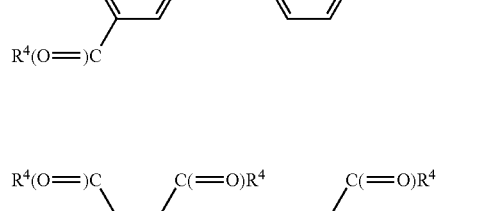
(II⁴₁₄)

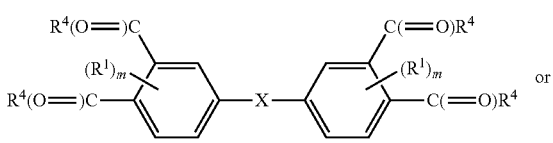
(II⁴₁₅) or

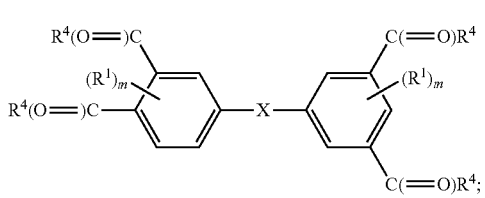
(II⁴₁₆)

preferably

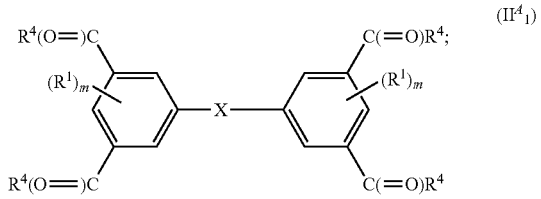
(II⁴₁)

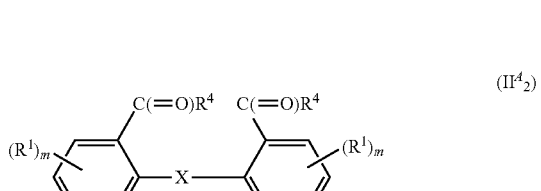
(II⁴₂)

or

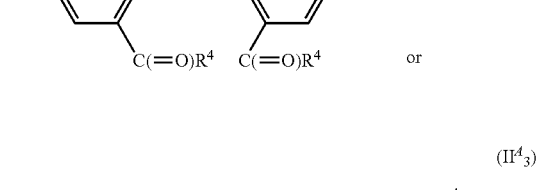
(II⁴₃)

preferably formula (II⁴₁); wherein m, R¹ and R⁴ are as defined above.

For any variant of the process described herein, among the bis-C₆aryl-containing tetradentate ligand precursors, mention may be made of precursors of any one of formulae (II⁴), (II⁴₁) through (II₁₆) as defined above; preferably ligand precursors of any one of formulae (II⁴), (II⁴₁), (II⁴₂) or (II⁴₃); wherein X represents a covalent bond, C=O, CH₂ or N=N (of conformation cis or trans, preferably trans, when X represents N=N); most preferably precursors of formula (II⁴) or (II⁴₁) wherein X represents CH₂.

Advantageously, in any one of the process variants described above, the bis-C₆aryl-containing tetradentate ligand precursor may have one of the following structures:

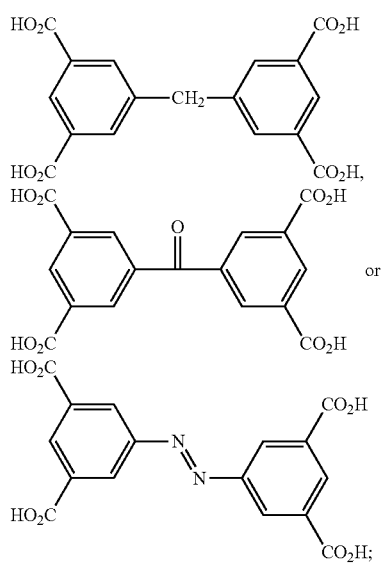

preferably

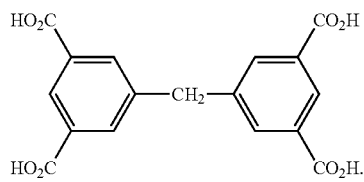

In a variant A, in any one of the process variants described above, step (i) may be carried out by first mixing formic acid and the bis-$C_6$aryl-containing tetradentate ligand precursor, for example of formula ($II^4$), either as such or in a suitable solvent; then adding the titanium precursor selected from $TiCl_4$, $TiO(acac)_2$, $TiOSO_4$ (titanyl sulfate), $Ti(SO_4)_2$ or a titanium alkoxide of formula (III) portion-wise (in several batches); followed by vigorous stirring and heating at a temperature between 100-150° C., preferably 120° C. for a suitable amount of time. Preferably the titanium precursor is a titanium alkoxide of formula (III) as defined in any of the variants described herein. In another variant $A_1$, formic acid is replaced by acetic acid. When the titanium precursor is in liquid form (such as $TiCl_4$ or certain titanium alkoxides), it may be added dropwise. When the titanium precursor is in solid form, it may be added stepwise in several consecutive batches.

In another variant B, in any one of the process variants described above, step (i) may be carried out by successively adding the bis-$C_6$aryl-containing tetradentate ligand precursor, for example of formula ($II^4$), the titanium precursor selected from $TiCl_4$, $TiO(acac)_2$, $TiOSO_4$ (titanyl sulfate), $Ti(SO_4)_2$ or a titanium alkoxide of formula (III), and then formic acid, at 25° C.±3° C.; followed by heating at a temperature between 80-120° C., preferably 100° C. for a suitable amount of time. Preferably the titanium precursor is a titanium alkoxide of formula (III) as defined in any of the variants described herein. In another variant $B_1$, formic acid is replaced by acetic acid.

In yet another variant C, in any one of the process variants described above, step (i) may be carried out under $1.10^5$ Pa (ambient pressure conditions) by successively adding the bis-$C_6$aryl-containing tetradentate ligand precursor, for example of formula ($II^4$), formic acid, and then the titanium precursor selected from $TiCl_4$, $TiO(acac)_2$, $TiOSO_4$ (titanyl sulfate), $Ti(SO_4)_2$ or a titanium alkoxide of formula (III); and let the reaction proceed at a temperature ranging between 25° C.±3° C. (room temperature) and the boiling temperature of the mixture (reflux) for a suitable amount of time. Preferably the titanium precursor is a titanium alkoxide of formula (III) as defined in any of the variants described herein. In another variant $C_1$, formic acid is replaced by acetic acid.

The process variants A, $A_1$, B, $B_1$, C and $C_1$ may be carried out in a suitable solvent. Preferably, the solvent is a polar solvent, or a mixture of two or more polar solvents. The polar solvents that may be used may especially be chosen from $H_2O$, acetic anhydride, sulfolane, $C_1$-$C_4$ alcohols, benzyl alcohol, chlorobenzyl alcohol, N,N-dimethylformamide (DMF), N,N-diethylformamide (DEF), dimethylsulfoxide (DMSO), ethylene glycol, dioxane, acetonitrile, acetone, tetrahydrofuran (THF), pyridine and N-methylpyrrolidone, or a mixture of two or more of those. Preferably, the polar solvents may especially be chosen from $H_2O$, acetic anhydride, and sulfolane, or a mixture of two or more of those. When $H_2O$ is used as the solvent or in the solvent mixture, it is preferably used in an amount that does not exceed 10 equivalents of Ti(IV).

Advantageously, in any one of the process variants described above, the precursor of formula (III) may be selected from titanium ethoxide, titanium isopropoxide, titanium n-propoxide or titanium butoxide, preferably titanium isopropoxide.

Advantageously, in any one of the process variants described above, within the reaction mixture, the titanium alkoxide of formula (III)/tetradentate ligand precursor of formula ($II^4$) molar ratio preferably varies from about 1.0 to 4.0 approximately and more preferably from about 2.3 to 3.3.

Optionally, in any one of the process variants described above, the reaction mixture used during the first step may also contain one or more additives chosen from monocarboxylic acids such as, for example, acetic acid and organic bases such as, for example, alkylamines for instance triethylamine. The presence of a monocarboxylic acid such as acetic acid allows to improve the crystallinity of the solid material in accordance with the invention and/or the yield of the reaction. The presence of such additives may also make it possible to decrease the duration of the synthesis. When they are used, these additives preferably represent from 1 to 10% by weight and more preferably still from 1 to 5% by weight relative to the total weight of the reaction mixture.

Advantageously, in any one of the process variants A, $A_1$, B, $B_1$, C or $C_1$ described above, the duration of the heating step will vary as a function of the temperature used, it being understood that the higher the temperature, the shorter this duration is. Preferably, the duration of the heating step in process variants A, $A_1$, B, or $B_1$, may vary from 50 to 100 hours approximately, preferably about 72 hours. Preferably, the duration of the heating step in process variant C may vary from 12 to 36 hours approximately, preferably about 24 hours.

Advantageously, in any one of the process variants described above, the process may further comprise a step of isolating the resulting titanium-based inorganic-organic hybrid solid material composed of a three-dimensional succession of building units of formula ($I^4$) wherein:

A represents a formate ligand $HCO_2^-$ or an acetate ligand $MeCO_2^-$; preferably a formate ligand $HCO_2^-$;

n represents the average number of water molecules that are coordinated to the titanium metal centers per building unit in the material; and L represents a bis-$C_6$aryl-containing tetracarboxylate ligand having the structure (II) as defined below;

and subjecting it to heat treatment at a temperature of 180-320° C., preferably 280° C. to form a titanium-based inorganic-organic hybrid solid material composed of a three-dimensional succession of building units of formula ($I^B$):

$$Ti_{12}O_{18}L_3 \quad (I^B)$$

wherein L represents a bis-$C_6$aryl-containing tetracarboxylate ligand having the structure of formula (II)

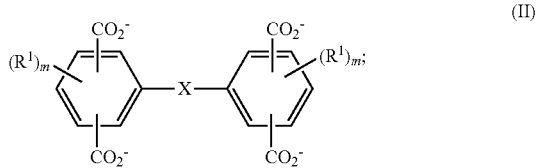

wherein X, m and $R^1$ are as defined above; preferably each occurrence of $R^1$ represents H; most preferably X represents $CH_2$ and each occurrence of $R^1$ represents H.

Advantageously, in any one of the process variants described above, the process may further comprise a step of isolating the resulting titanium-based inorganic-organic hybrid MOF material composed of a three-dimensional succession of building units of formula ($I_0$), (I) or ($I^4$) wherein:

A represents a formate ligand $HCO_2^-$ or an acetate ligand $MeCO_2^-$; preferably a formate ligand $HCO_2^-$;

n represents the average number of water molecules that are coordinated to the metal centers per building unit in the material; and L represents a bis-$C_6$aryl-containing tetracarboxylate ligand having the structure (II) as defined above;

and reacting it with HCl, $H_2SO_4$, $H_3PO_4$, $R^2$—$SO_3H$, or $R^2$—$PO_3H_2$, wherein $R^2$, for each occurrence, independently represent OH, $C_{1-12}$ alkyl, $C_{1-12}$ heteroalkyl, $C_{6-10}$aryl, $C_{5-10}$ heteroaryl; where each of the foregoing alkyl and heteroalkyl moiety may be linear or branched and cyclic or acyclic.

Alternatively, the formate/acetate ligands may be removed thermally under vacuum (below 200° C., for example a temperature ranging from 20 to 200° C., preferably from 50 to 150° C.) and the resulting material may then be exposed to air moisture at a temperature below 100° C., for example from 20 to 100° C., or room temperature (25° C.±3° C.). This alternative process effectively results in the replacement of the formate/acetate ligands by $OH/H_2O$ ligands.

In yet another variant, the formate/acetate ligands may be removed thermally under vacuum (below 200° C., for example a temperature ranging from 20 to 200° C., preferably from 50 to 150° C.) and the resulting material may then be exposed to a vaporized organic compound at temperature below its boiling temperature, for example room temperature (25° C.±3° C.). Preferably, the organic compound contains at least one polar functional group such as amines, carboxylic groups, phenols . . . . This alternative process effectively results in the replacement of the formate/acetate ligands by other polar organic ligands.

In yet another alternative, post-synthetic functionalization may be effected, through a solvothermal treatment, by post-synthetically grafting other molecules having a polar group (e.g. amines, carboxylic groups, phenols . . . ) on the metal sites of the titanium-based inorganic-organic hybrid solid material composed of a three-dimensional succession of building units of formula ($I_0$), (I) or ($I^4$) wherein A represents a formate ligand $HCO_2^-$ or an acetate ligand $MeCO_2^-$; preferably a formate ligand $HCO_2^-$, directly through the replacement of the formate or acetate ligands. In these cases, one might not need to use large excesses of the molecules to be anchored but more likely stoichiometric excesses. For example, the reader may refer to the work by Serre et al. with MIL-101(Cr), [11] and adapt the methods described therein to effect similar post-synthetic graft with the Ti-based MOFs according to the present invention.

Advantageously, in any one of the process variants A, $A_1$, B, $B_1$, C or $C_1$ described above, prior to adding the titanium precursor selected from $TiCl_4$, $TiO(acac)_2$, $TiOSO_4$ (titanyl sulfate), $Ti(SO_4)_2$ or a titanium alkoxide of formula (III), another metallic inorganic precursor in the form of a metal $M_1$, a salt of a metal $M_1$ of formula (IV) or a hydroxide or oxide of a metal $M_1$, is added to the reaction mixture;

$$M_1Y_p \cdot nH_2O \quad (IV)$$

wherein $M_1$ is a metal selected from Cu, Fe, Co, Ni, Mn, V, Cr, Ru, Sn or Nb; and Y represents $Cl^-$, $NO_3^-$, $SO_4^{2-}$, $AcO^-$, or

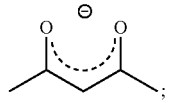

preferably the other metallic inorganic precursor is in the form of a salt of $Cu^{2+}$, $Fe^{2+}$, $Fe^{3+}$, $Co^{2+}$, $Co^{3+}$, $Ni^{2+}$, $Mn^{2+}$, $Mn^{3+}$, $Mn^{4+}$, $V^{3+}$, $V^{4+}$, $Cr^{3+}$, $Ru^{3+}$, $Ru^{4+}$, $Sn^{4+}$, $Nb^{4+}$ or $Nb^{5+}$; most preferably the other metallic inorganic precursor is a metal salt such as $RuCl_3$, $VCl_3$, $SnCl_4$, $CrCl_3$ or $FeCl_3$.

Alternatively, metal doping may be effected post-synthetically by replacing a subset of the Ti(IV) metal centers in the Ti-based MOF materials of the invention with other metal ions, such as Sn(IV), Nb(V) and Nb(IV). For example, the reader may refer to the work by Cohen et al. [12] and adapt the methods described therein to effect similar post-synthetic metal doping with the Ti-based MOFs according to the present invention.

As such, metal ions such as $Cu^{2+}$, $Fe^{2+}$, $Fe^{3+}$, $Co^{2+}$, $Co^{3+}$, $Ni^{2+}$, $Mn^{2+}$, $Mn^{3+}$, $Mn^{4+}$, $V^{3+}$, $V^{4+}$, $Cr^{3+}$, $Ru^{3+}$, $Ru^{4+}$, $Sn^{4+}$, $Nb^{4+}$ or $Nb^{5+}$, may be incorporated into the material's structure in place of Titanium metal centers.

The metal doping ratio may be adjusted by using different amounts of starting metal salt to prepare the titanium-based material according to the invention (see infra). As such, the % doping is tunable and may range from 1% to 20% of the aforementioned metal centers. Generally, the doped Ti-based material may have the same crystal structure as the pure Ti-based material (no doping). However, they may be slight differences in unit cell parameters.

Any one of the process variants described above allows the preparation of a crystalline titanium-based inorganic-organic hybrid MOF material having an oxo to metal ratio (oxo to Ti ration in case of pure Ti-based MOFs) >1.0, preferably ≥1.1, most preferably ≥1.2.

As such, in yet another aspect, there is provided a titanium-based inorganic-organic hybrid solid material having an oxo to metal ratio (oxo to Ti ration in case of pure Ti-based MOFs) >1.0, preferably ≥1.1, most preferably ≥1.2; obtainable by any one of the process variants described herein.

In any one of the process variants described above, the resulting solid material may be isolated by any separation method known to a person skilled in the art, among which filtration is preferred, optionally under reduced pressure.

In any one of the process variants described above, when the synthesis is complete, the solid material may be washed, either very rapidly statically, or by redispersion in a solvent at ambient temperature (25° C.±3° C.) with stirring, for example with an organic solvent such as for example DMF or ethanol, then dried by any appropriate drying technique known to a person skilled in the art. This drying step makes it possible to eliminate any trace of solvent. For example, it may be carried out by calcination of the solid material in air or under vacuum, at a temperature of 100 to 200° C. for 3 to 48 hours, preferably of 10 to 15 hours. In the case of titanium-based inorganic-organic hybrid solid material composed of a three-dimensional succession of building units of formula ($I^B$), the drying may be carried out at higher temperature of 180-320° C., preferably 280° C.

As a whole the high condensation degree Ti-based MOF materials according to the present invention possess several unique chemical and structural features as summarized below:
  Green solvent, reflux reaction condition, easy to scale-up
  Excellent chemical stability under different conditions compared to other Ti-MOFs known in the art
  Rigid permanent porosity with diverse active modifiable sites for further multi-functionalization
  In the LT form (LT for Low Temperature) or $Ti_{12}O_{15}L_3A_6 \cdot nH_2O$ ($I^A$) (such as $Ti_{12}O_{15}L_3$ (formate)$_6 \cdot nH_2O$ (n~6-7; L=mdip=5,5'-methylenediisophthalic acid or [(HO$_2$C)$_2$—C$_6$H$_2$—CH$_2$—C$_6$H$_2$—(CO$_2$H)$_2$])), a $Ti_{12}O_{15}$ oxocluster building unit with a high oxo to Ti ratio (close to 1.2), as well as the possibility (after acid treatment) to either access acid sites (Lewis, Bronsted) and/or functionalization with acid groups. Other types of post-synthetic modifications are also possible.
  In the HT form structure (HT for High Temperature) or $Ti_{12}O_{18}L_3$ ($I^B$) (such as $Ti_{12}O_{18}L_3$ (L=mdip)), an inorganic building unit that consists of ca. 1.1 nm width $TiO_{1.5}$ infinite nanorods, reminiscent of $TiO_2$ Other advantages may also emerge to those skilled in the art upon reading the examples below, with reference to the attached figures, which are provided as nonlimiting illustrations.

EQUIVALENTS

The representative examples that follow are intended to help illustrate the invention, and are not intended to, nor should they be constructed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art.

The following examples contain important additional information, exemplification and guidance that can be adapted to the practice of this invention in its various embodiments and the equivalents thereof.

EXAMPLES

The Ti-based materials according to the present invention and their preparation can be understood further by the examples that illustrate some of the processes by which these conjugates are prepared or used. It will be appreciated, however, that these examples should not be construed to limit the invention. Variations of the invention, now known or further developed, are considered to fall within the scope of the present invention as described herein and as hereinafter claimed.

Example 1—Preparation of $Ti_{12}O_{15}L_3$ (Formate)$_6 \cdot nH_2O$ (n~6-7; L=mdip=5,5'-Methylenediisophthalic Acid) Also Referred to Herein as "LT Ti-mdip MOF"

In general, the reaction of Ti(iPrO)$_4$ and 5,5'-methylenediisophthalic acid (H$_4$mdip) in formic acid produces the LT Ti-mdip MOF, as shown in Scheme 1 below.

Scheme 1

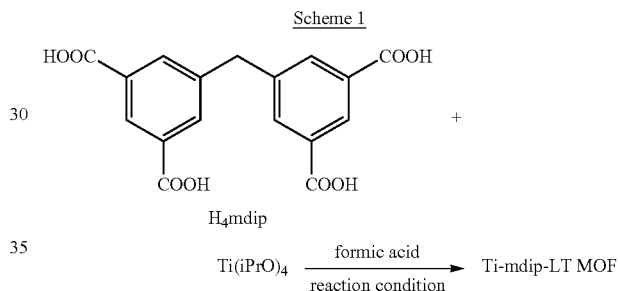

A detailed synthesis is described in the following three methods A, B and C.

In both methods A and B, reactions were carried out under solvothermal conditions in sealed reactors. The generated pressure of the reaction mixture during heating is normally higher than standard atmospheric pressure.

In contrast, method C is based on reflux condition in open reaction system under standard atmospheric pressure, which is much safer and easier to handle and is more readily applicable for larger scale production. The method may be adapted for the desired amount of target LT Ti-mdip MOF by merely selecting a reflux apparatus of appropriate size. Thus method C is particularly suited for industrial scale production, as it meets well with the industrial requirements.

Method A:

To a 23 mL Teflon reactor, H$_4$mdip (100 mg, 0.29 mmol) and formic acid (5 mL) were added and stirred at room temperature until the solid dispersed uniformly. Ti(iPrO)$_4$ (200 µL, 0.66 mmol) was added dropwise while the mixture was stirred violently, avoiding forming large pieces of white precipitate. The mixture was kept stirring at room temperature for 30 minutes. And then it was sealed in an autoclave and heated in an oven for 72 hours at 120° C. After cooled to room temperature, the white solid product was filtered with reduced pressure and washed with ethanol (EtOH).

Method B:

To a 25 mL glass vial, H$_4$mdip (100 mg, 0.29 mmol), Ti(iPrO)$_4$ (200 µL, 0.66 mmol) and formic acid (5 mL) were added successively and stirred at room temperature for 30 minutes. Then the vial was tightly sealed with cap and was heated in an oven at 100° C. for 72 hours.

Method C:

To a 25 mL round bottom flask, H$_4$mdip (200 mg, 0.58 mmol), formic acid (10 mL) and Ti(iPrO)$_4$ (400 μL, 1.32 mmol) were added following the above order. The reaction mixture was kept under reflux condition for 24 hours. Large scale synthesis (such as 10 g or 20 g scales, or more) could be easily achieved with this method. The synthesis of 100 g scale of product has been successfully carried in a one-pot reaction without notable difference of the physical and chemical properties of the product.

Example 2—Preparation of Ti$_{12}$O$_{18}$L$_3$ (L=mdip), also referred to herein as "HT Ti-mdip MOF"

The LT Ti-mdip MOF solid of Example 1 (200 mg) was grinded into fine powder and was transferred into a petri dish, dispersed uniformly forming a thin layer. Afterwards it was kept at 280° C. for 12 hours under air atmosphere, resulting in dark yellow powder, which is the product of HT form structure. The same calcination procedure could also be carried on large scale, such as 5 g and 10 g, without notable difference of the obtained product quality.

Example 3—Preparation of Quartz Plate Supported Ti-mdip Films

To a 50 mL conical flask, H$_4$mdip (100 mg, 0.29 mmol), Ti(iPrO)$_4$ (200 μL, 0.66 mmol) and formic acid (25 mL) were added successively and stirred at room temperature for 30 minutes. Magnetic stirring bar was removed and quartz plates were added into the mixture. The reaction was kept reflux for 24-48 hours monitored by checking powder X-ray diffraction pattern on the powder product. Quartz plate supported MOF films were collected as soon as the reaction was completed and washed with EtOH. The LT structure film was dried under air overnight before any further characterizations. HT structure film was obtained by heating the LT film under 280° C. for 6 hours. Besides quartz, other substrates, including normal glass, TiO$_2$, Au, Pt . . . , also work well to support the growth of Ti-mdip films. Further, the crystal orientation and arrangement of the MOF nanoparticles could be rationally tuned by the component nature of the substrate.

Example 4—Crystal Structure Characterization

Both crystal structures of low temperature form (LT) of Example 1 and high temperature form (HT) of Example 2 of the Ti-mdip MOF were solved with high resolution powder X-ray diffraction data assisted by DFT calculation.

Both LT (Example 1) and HT (Example 2) product samples were grinded into fine powder and sealed in glass capillaries with inner diameters of 0.3 mm and 0.7 mm for the LT and HT forms, respectively. PXRD pattern of LT was collected on a Bruker D8 diffractometer at room temperature for 72 hours in a 2θ range from 3-90° (step size of 0.01°). Synchrotron data of the HT were collected at Soleil on the crystal beamline in a 2θ range from 1-50° (step size of 0.002). The quartz supported MOF films of both LT and HT structures were placed on a round aluminum sample holder and the corresponding PXRD patterns were recorded on a conventional high resolution (θ-2θ) Siemens D5000 diffractometer at room temperature for 61 hours in a 2θ range from 3-10° (step size of 0.02°, 630 seconds/step). As shown in FIG. 1, it is clear that some X-ray diffraction Bragg peaks of the HT structure have a notable shift to higher 2θ angle range, in agreement with a decrease in unit cell parameters compared to those of the LT structure.

Quartz plate supported MOF films both have a thickness of around 300 nm. Their X-ray powder diffraction peaks (inserted figure) showed much less intensity in comparison with those of the bulk materials. There is a slight shift to higher 2θ angle of the Bragg peaks in both cases due to the quartz plate thickness of 1 mm.

Figure 9A:
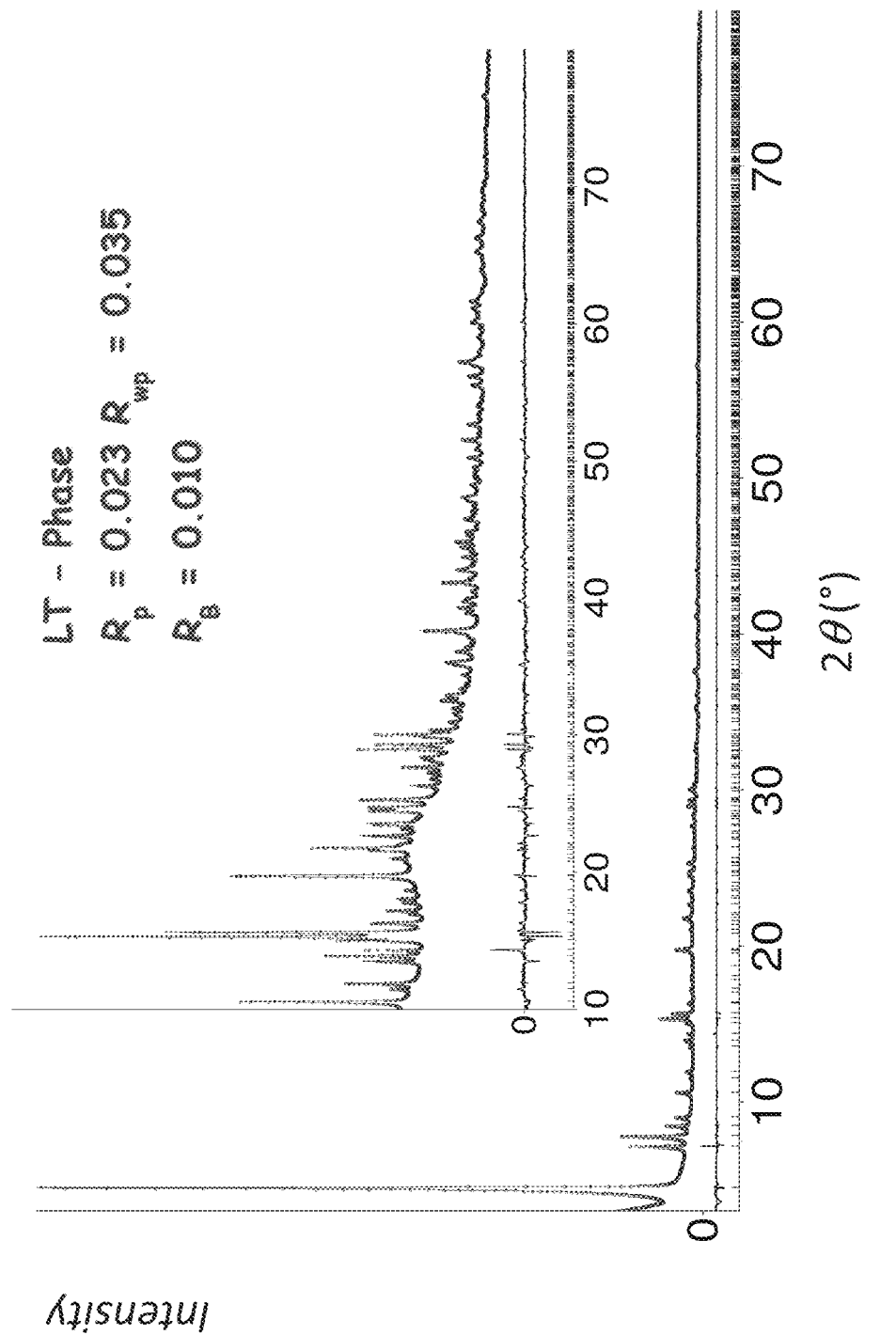
FIG. 9A shows a final Rietveld plot of the LT form of Ti-based MOF solid according to the invention, obtained in Example 1.
Figure 9B:
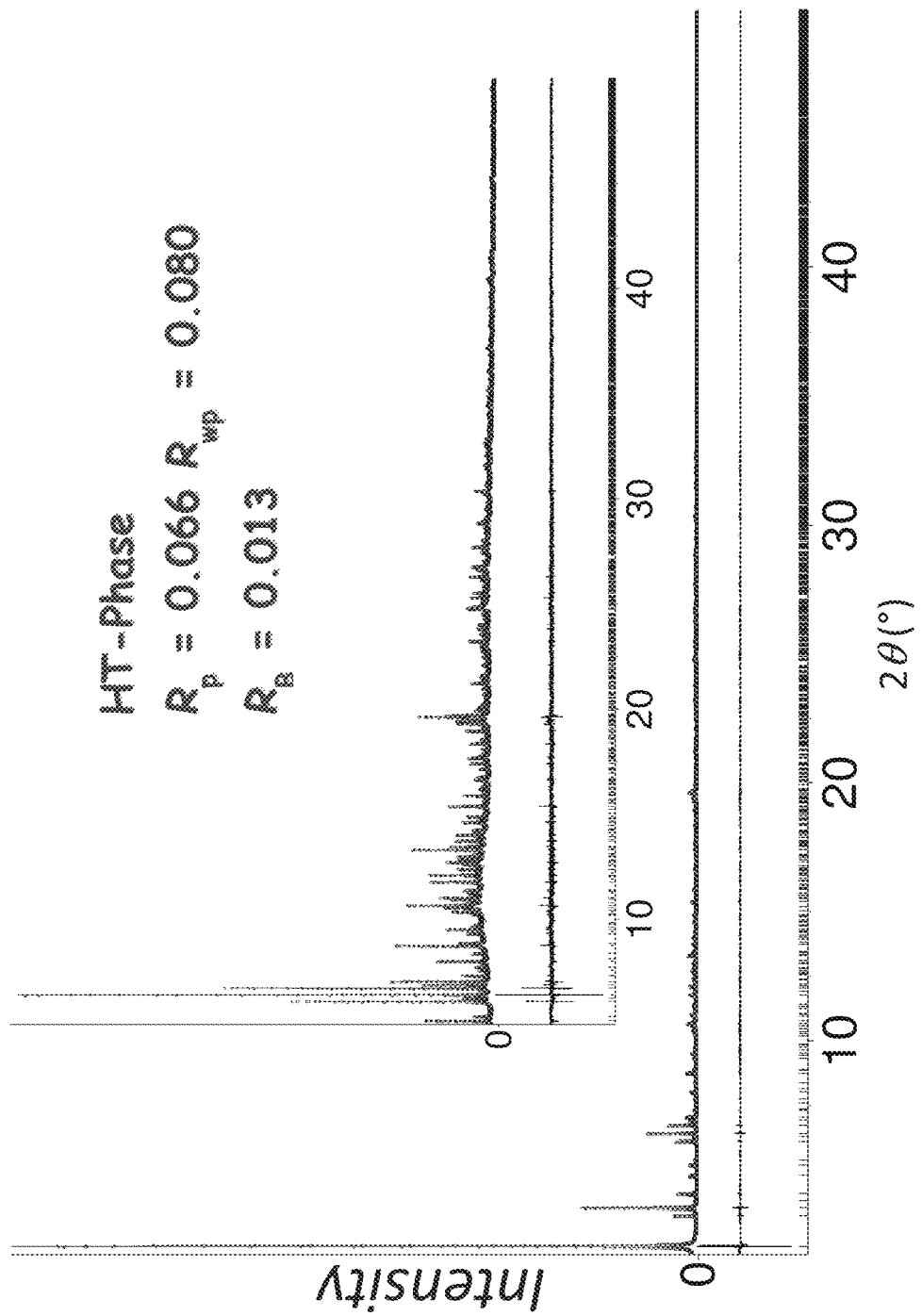
FIG. 9B shows a final Rietveld plot of the HT form of Ti-based MOF solid according to the invention, obtained in Example 2.

Rietveld plots were obtained for both LT and HT forms (FIGS. 9A and 9B, respectively) using TOPAS program. The Rietveld plots show that the simulated diagram has a very good consistence with the experimental data, as well as the $R_p$, $R_{wp}$ and $R_B$ parameters are in a good range, supporting the location of the atoms and determination of the MOF structures are quite accurate and reliable.

Figure 2:
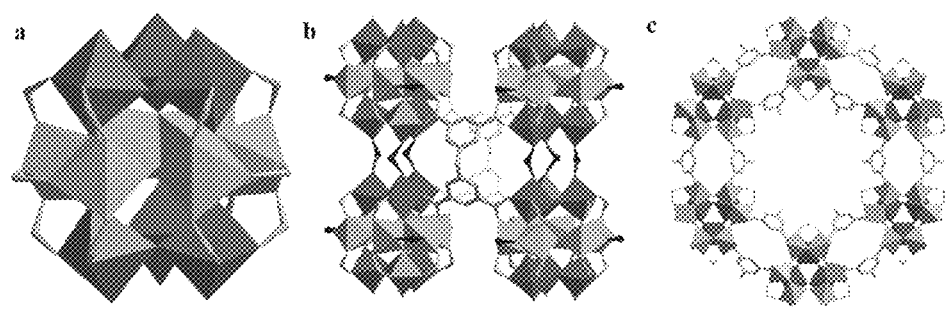
FIG. 2 shows the crystal structure of the LT form of Ti-based MOF solid according to the invention, obtained in Example 1.

The LT framework is built of Ti$_{12}$O$_{15}$ oxocluster secondary building units (SBUs), which are interconnected by H$_4$mdip linker molecules and formate groups serving as both terminal and bridging secondary ligands. As shown in FIG. 2a, typically in one Ti$_{12}$O$_{15}$ oxocluster SBU, six distorted Ti(IV) octahedrons interlinked with each other by μ2O groups forming a hexamer which stays in the middle. Then the hexamer is sandwiched by two trimers of Ti(IV) octahedra at its top and bottom separately by sharing μ3O groups and linker carboxylate groups for connections. The adjacent SBUs are interconnected by the linker molecules to build up the 3D framework (FIG. 2b). It is noteworthy that there are two kinds of coordinated formate groups (marked in blue). The first one is bridging between two Ti$_{12}$O$_{15}$ oxocluster SBUs along the c-axis acting as the secondary ligand. The other one is the terminal species facing the major channel of the structure. The LT compound has a nano-size (free diameter of about 1.1 nm) channel when viewed along the c-axis (FIG. 2c), providing considerable space for further functionalization and application.

Figure 3:
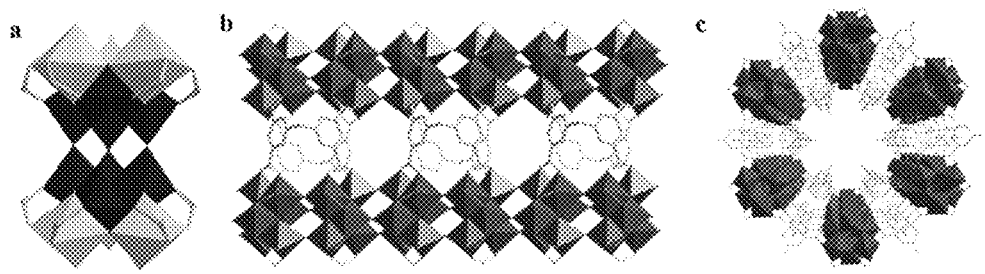
FIG. 3 shows the crystal structure of the HT form of Ti-based MOF solid according to the invention, obtained in Example 2.

The HT form structure was obtained by heating the LT form compound at 280° C. During the calcination all the coordinated formate groups were thermally removed and rearrangement of Ti(IV) octahedra of the hexamer in the LT building unit took place generating two new trimers. These two new trimers connect the two original Ti(IV) octahedral trimers at the top and bottom (FIG. 3a) resulting in an infinite Ti-oxo chain with a Ti/oxo ratio of 1/1.5, which is reminiscent to the pure inorganic TiO$_2$ composition (½). The adjacent Ti-oxo rods are running along the c-axis connected by the organic linker molecules (FIG. 3b), which yields the similar 3D porous structure as the LT form (FIG. 3c).

The crystal structure information of both LT and HT forms is provided in FIG. 10.

Figure 4:
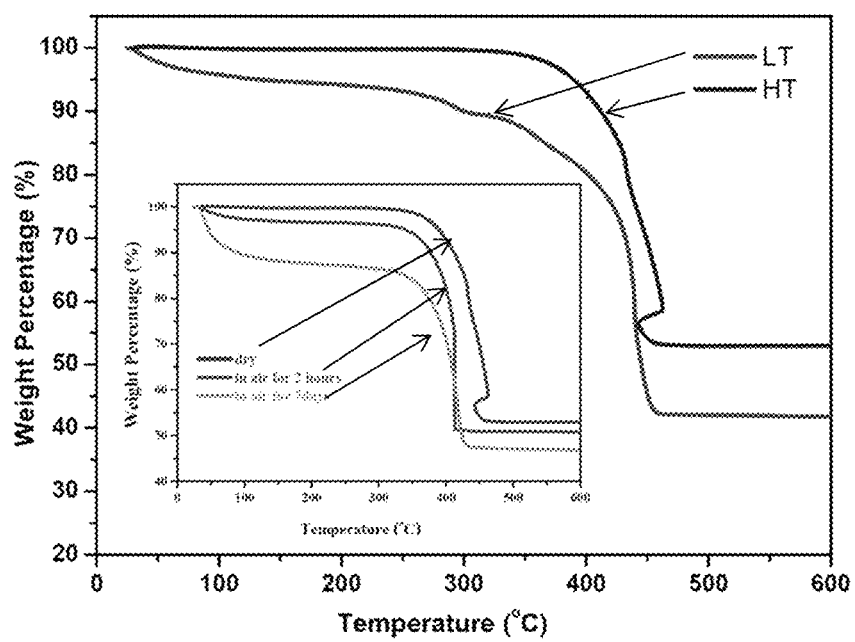
FIG. 4 shows the Thermal gravimetric analysis under oxygen atmosphere of both LT and HT forms of Ti-based MOF solids according to the invention, obtained in Examples 1 and 2, respectively.

Example 5—Characterization Results a) Thermal Stability (FIG. 4)

Thermogravimetric analyses were carried out with a Mettler Toledo TGA/DSC 1, STAR System apparatus under an O$_2$ flow of 50 mL/min, at a heating rate of 3° C./min to 600° C. For the LT form (in red), continuous weight loss upon heating was found in the temperature range of 25° C. to around 350° C., which correspond to free solvent molecules (formic acid and water) and coordinated formate species (terminal formates facing the channel running along the c-axis and bridging formates which connect the adjacent Ti$_{12}$-oxocluster SBUs along the c-axis) respectively. The departure of the organic linker and related MOF structure decomposition took place when the temperature was above 350° C., resulting in TiO$_2$ as the final inorganic residue. In contrast the HT compound (in blue) did not show any weight loss from the beginning until 375° C. with a wide range plateau suggesting the accessible void cavity in the MOF structure.

Figure 5:
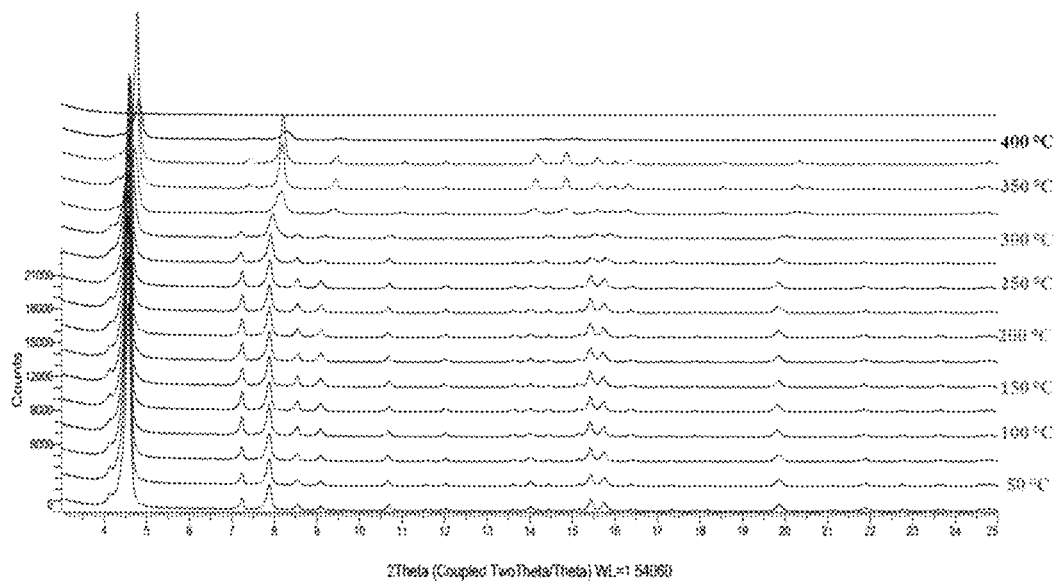
FIG. 5 shows temperature-dependent powder X-ray diffraction patterns of LT form of Ti-based MOF solid according to the invention, obtained in Example 1.

As shown in the inserted figure, the HT form sample adsorbed water molecules slowly when it was taken out from the calcination oven and exposed in air. 5% of guest water molecules were detected when the dry sample was let in air for 2 hours (in green) while 13% of water was determined for the sample stayed in air for 7 days (orange curve). The relatively much slower adsorption of water of HT in air compared to some reported hydrophilic MOFs, such as MIL-53, $NH_2$-MIL-125 and MIL-160, evidenced the hydrophobic environment of the porosity in HT structure.

b) Temperature-Dependent X-Ray Powder Diffraction (FIG. 5)

Figure 6:
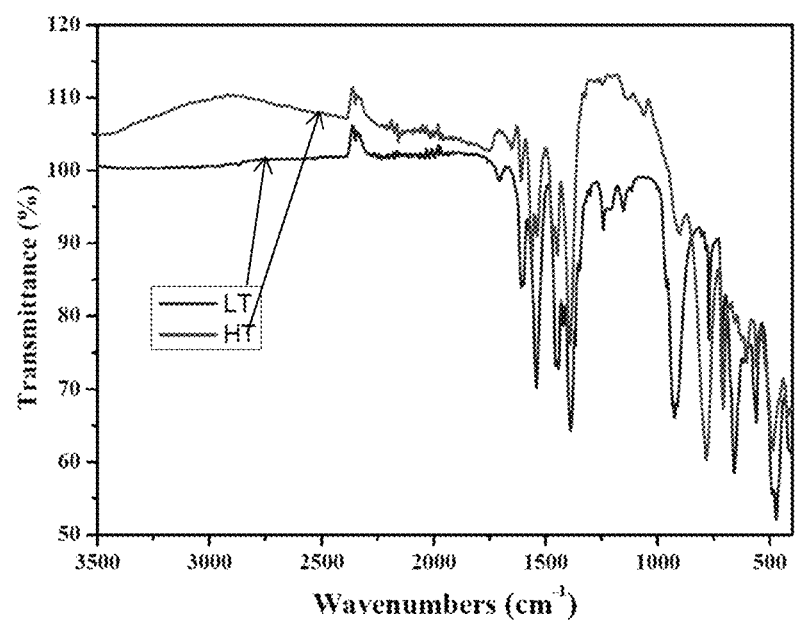
FIG. 6 shows Infra-Red (IR) spectra of both LT and HT forms of Ti-based MOF solids according to the invention, obtained in Examples 1 and 2, respectively.

X-ray temperature dependent diffraction experiment was performed on a Bruker-D8 Advance diffractometer equipped with a HTK-1200N (Anton Parr) high-temperature chamber furnace and a LYNXEYE XE detector (with Cu-Kα radiation). PXRD patterns were collected every 25° C. from room temperature to 500° C. As shown in the above temperature-dependent PXRD patterns, the LT form structure could be stable without notable change below 300° C. in the heating chamber with 2 hours scan for each temperature step. Afterwards the phase change to HT form structure took place and was completed slowly upon heating. The HT structure has a thermal stability up to around 400° C. and then decomposition of the MOF framework was found.

c) Infrared Spectroscopy (IR) (FIG. 6)

Figure 7A:
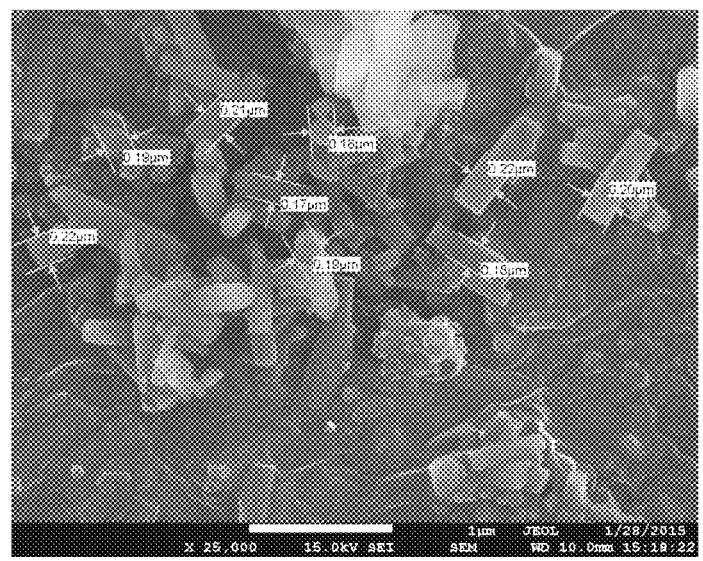
FIG. 7A shows a scanning electron microscopy (SEM) image of LT form of Ti-based MOF solid according to the invention, obtained in Example 1 by method B.
Figure 7B:
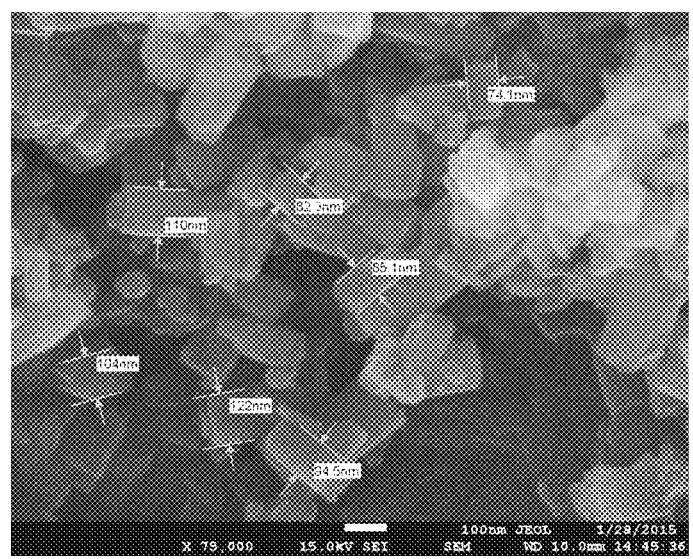
FIG. 7B shows a scanning electron microscopy (SEM) image of LT form of Ti-based MOF solid according to the invention, obtained in Example 1 by method C.

IR spectra were measured with a Nicolet 6700 FTIR thermoscientific spectrometer between 400 and 4000 $cm^{-1}$. As shown in FIG. 6, the peaks in the range from 1700 to 1200 $cm^{-1}$ for both LT and HT forms are very close despite slight difference of relative transmittances of few peaks, suggesting the similarity of chemical environment and connection fashion for the organic linker in both structures. However, the lower wavenumber range from 1000 to 500 $cm^{-1}$ is comparably more complicated. Notable differences between the two samples could be observed possibly due to the inner SBU connection arrangement and change of the oxo groups.

d) Scanning Electron Microscopy (SEM) (FIGS. 7A and 7B)

Figure 8:
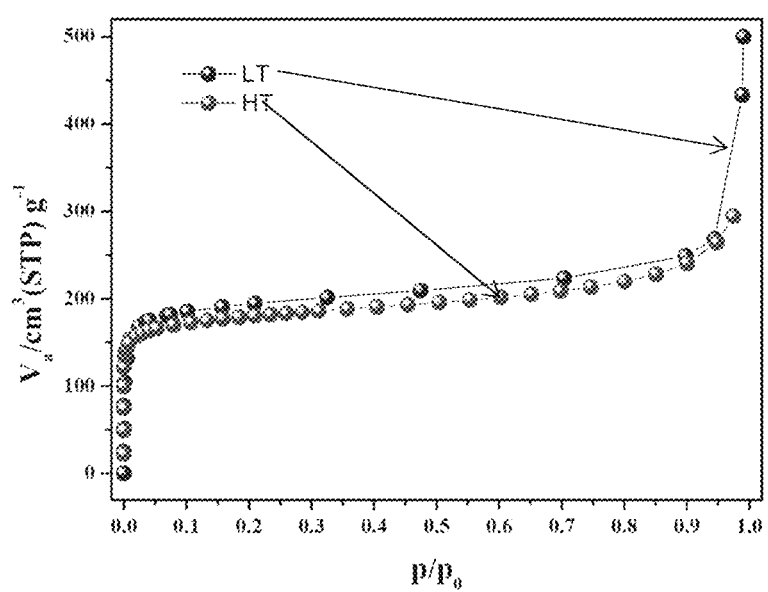
FIG. 8 shows nitrogen adsorption porosimetry measurements (77K) of both LT and HT forms of Ti-based MOF solids according to the invention, obtained in Examples 1 and 2, respectively.

SEM images were taken with a JEOL JSM-7001F microscope using gold coated samples. The SEM images of Ti-mdip-LT products obtained under solvothermal condition (FIG. 7A) method B and reflux (method C) (FIG. 7B) review that the microcrystals have a hexagonal column morphology which corresponds well with its P6/mmm hexagonal space group crystal structure. Products achieved with both methods have good size and shape distributions. The MOFs prepared in reflux condition have a smaller size (100±20 nm of the diameter for the hexagonal cross profile) than those obtained in solvothermal condition (200±20 nm in diameter of hexagonal cross profile). It is noteworthy that the sizes of all the MOF products are already in nano-material scale which is really helpful for following applications in different aspects.

e) Nitrogen Porosimetry (FIG. 8)

Nitrogen adsorption measurements were performed with a BEL Japan Belsorp Mini apparatus at 77 K after the sample being fully activated (BEL Japan, BELSORP Prep). The LT and HT samples were directly activated thermally at 230° C. and 120° C. separately for 20 hours under vacuum before the nitrogen adsorption at 77K were carried out. The HT sample is obtained by heating the LT sample at 280° C. for 12 hours during which all the guest molecules in the porosity of the MOF have been completely removed. Thus for the nitrogen adsorption tests, activation at 120° C. is enough to remove the only guest water molecules adsorbed in air. LT sample is as-made product without any activation. Thermal activation at high temperature is needed to remove as much as possible the guest molecules. The Brunauer-Emmett-Teller (BET) surface area, Langmuir surface area and total pore volume ($p/p_0$=0.990) of the LT sample were calculated to be 760 $m^2/g$, 800 $m^2/g$ and 0.74 $cm^3/g$ respectively. For the HT sample, after removal of formates and rearrangement of the framework connection, the major channel running along the c-axis contracted a little bit, which corresponds well with the decreased value of the BET surface area, Langmuir surface area and total pore volume ($p/p_0$=0.990) of the HT sample to 690 $m^2/g$, 780 $m^2/g$ and 0.46 $cm^3/g$ respectively.

f) Chemical Stability Tests

The Ti-mdip MOFs of Examples 1 and 2 have excellent stability in water, concentrated HCl (37%), concentrated $HNO_3$ (65%), concentrated $H_2SO_4$ (98%) and even $H_3PO_4$ with high concentration (6 M) at room temperature. After soaking the MOF solid of Examples 1 and 2 in the above chemicals for a least one week, there was no notable difference in their PXRD patterns observed. The compound also shows good tolerance in basic aqueous condition, such as NaOH/$NaHCO_3$ buffer with pH=10. The crystallinity of the MOF was mostly kept after five days. Furthermore, when the MOF compound of Examples 1 and 2 was refluxed in boiling water it showed considerable resistance and could resist to degradation for more than 24 hours, suggesting acceptable hydrothermal stability. Therefore, compared to the benchmark material of $NH_2$-MIL-125, Ti-mdip MOF of Examples 1 and 2 have notably much better stability towards various chemical conditions.

Example 6 Post-Synthesis Functionalization

Both organic and inorganic parts of the Ti-mdip MOFs of Examples 1 and 2 could be easily modified and thus introduction of different functionalities into the MOF becomes possible. The organic formate species of the LT form could be replaced by ionic groups with various functional groups through simple soaking and exchange while the inorganic $Ti_{12}O_{15}$ oxocluster building unit could be doped with a wide range of metal atoms under in situ reaction condition. Post metal exchange of the Ti-mdip building unit was also carried out: tetravalent metal ions, such as Sn, Nb . . . , could be efficiently introduced into the Ti-mdip building unit by replacing the Ti ion in place. Also the doped metal ratio could be adjusted from 1%-25% by varying the concentrations of the tetravalent metal ions solutions.

a) In Situ Doping of the Ti-MOF Building Unit

A general procedure to dope metal atom into the building unit of the LT form of Example 1 is as follows: In a 50 mL round bottom flask, $H_4$mdip linker powder was dispersed in formic acid at room temperature with magnetic stirring for 10 minutes. Then a certain amount of the metal salt (NB: metal different than Ti) was added into the flask and mixed uniformly for another 30 min due to the weaker interaction between carboxylate groups with the other metal ions over Ti(IV). Afterwards Ti(iPrO)$_4$ was added dropwise to avoid forming large precipitates. The reaction mixture was stirred at room temperature for 20 minutes and kept under reflux condition for required time. The successful dopants cover a wide range of metals, including Cu, Co, Ni, Mn, V, Cr, Fe, Ru, Sn and Nb. Other metal species could be introduced into the Ti oxocluster by adjusting the reaction parameters. In addition, the dopant ratio could be adjusted by adding different amounts of starting metal salt put in the reaction. The loading is tunable and ranges from 1% to 20% for different metals. It should be noted that all the doped samples have the same crystal structure as the Ti-mdip MOF, albeit some slight difference in unit cell parameters. The dopant content and unit cell parameters of some selected doped samples are listed in Table 2 below. Note that upon thermal transformation from LT to HT form, one can therefore access easily to the corresponding doped HT form. In addition, the calcination treatment of each system may be adapted according to the % doping and the nature of the metal dopant.

Table 2 Doped Sample Information

| dopant | Metal salt | Loading (%)[a] | a = b (Å) | c (Å) | V (Å$^3$) |
|---|---|---|---|---|---|
| Ru | RuCl3 | 0.8 | 22.473 | 12.264 | 5364.010 |
| Ru | RuCl3 | 3 | 22.408 | 12.260 | 5331.085 |
| Ru | RuCl3 | 5.8 | 22.475 | 12.256 | 5361.223 |
| V | VCl3 | 8.3 | 22.467 | 12.312 | 5382.08 |
| V | VCl3 | 15.8 | 22.474 | 12.263 | 5364.00 |
| Sn | SnCl4 | 20.3 | 22.716 | 12.449 | 5563.31 |
| Cr | CrCl3 | 9.9 | 22.500 | 12.274 | 5381.00 |
| Fe | FeCl3 | 15.3 | 22.496 | 12.281 | 5382.39 |

[a]atomic molar ratio determined by EDS measurement.

b) Post-Functionalization by Acid Exchange

The formate groups in the Ti-based MOF structures according to the invention of both terminal and bridging coordination modes can be efficiently removed by treating the formate-containing MOF sample in different acid solutions. For instance, —OH groups or water molecules can be introduced at the formate positions when the MOF sample was treated with HCl solution. This is of a strong interest since it could lead to accessible Ti—OH and Ti—H$_2$O sites; in the latter case, this is known in the MOF chemistry that these terminal water molecules can easily be replaced by polar or quadrupolar guests or be evacuated under vacuum and/or thermal treatment. This confers therefore to the Ti-mdip LT form not only Bronsted but accessible Lewis acid sites, which are relevant for many applications particularly separation or catalysis, among others.

Besides, —HSO$_4$ and —H$_2$PO$_4$ ions replaced the formate ligands in H$_2$SO$_4$ and H$_3$PO$_4$ solutions, respectively. Furthermore, different organic functional groups could be grafted onto the MOF structure by using sulfonic acids with various organic moieties (pyridine, amine, camphor . . . ) generating diverse chemical environments insides the MOF porosity. These introduced functional groups were proved to not only enhance the stability of the MOF framework, but also improve its performance in some specific physical property test. For example, the H$_3$PO$_4$ post-treated sample shows much better stability in boiling water and basic solution. The H$_2$SO$_4$ treated sample might exhibit a higher proton conductivity than the pure LT compound does.

A general procedure for acid post-treatment and functionalization is detailed below:

To a 100 mL round bottom flask, Ti-mdip-LT powder of Example 1 (500 mg) was added firstly. And then the acid solution (50 mL) was added and the mixture was stirred at room temperature for 24 hours. The modified material was collected after filtration, washing with large amount of solvent (such as water, ethanol and DMF . . . ) and air dry.

The introduction of different organic moieties could be achieved by following the above procedure in solutions of sulfonic acids with different functional groups, including sulfanilic acid, pyridine-3-sulfonic acid, (1R)-(–)-camphor-10-sulfonic acid, hydroxylamine-O-sulfonic acid, 3-aminopropane-1-sulfonic acid, 4-hydrozinobenzenesulfonic acid, 5-sulfosalicylic acid, isoquinoline-5-sulfonic acid. Other sulfonic acid derivatives may be used in a similar fashion, as well as phosphonic acid derivatives.

While we have described a number of embodiments of this invention, it is apparent that our basic examples may be altered to provide other embodiments that utilize the Ti-based MOFs and methods of this invention. Therefore, it will be appreciated that the scope of this invention is to be defined by the appended claims rather than by the specific embodiments that have been represented by way of example.

LIST OF REFERENCES

[1] Victor W. Day, Todd A. Eberspacher, Yuewu Chen, Jinling Hao, Walter G. Klemperer, *Inorganica Chimica Acta* 229 (1995) 391-405

[2] Charles F. Campanap Yuewu Chen, Victor W. Day, Walter G. Klemperer and Robert A. Sparks, *J. Chem. Soc., Dalton Trans.*, 1996, Pages 691-702

[3] Galo J. de A. A. Soler-Illia,a Emmanuel Scolan,a Audrey Louis,a Pierre-Antoine Albouyb and Sanchez; *New J. Chem.*, 2001, 25, 156-165

[4] a) Shuai Yuan, Tian-Fu Liu, Dawei Feng, Jian Tian, Kecheng Wang, Junsheng Qin, Qiang Zhang, Ying-Pin Chen, Mathieu Bosch, Lanfang Zou, Simon J. Teat, Scott J. Dalgarnoc and Hong-Cai Zhou, *Chem. Sci.*, 2015, 6, 3926-3930; b) Amarajothi Dhakshinamoorthy, Abdullah M. Asiri, and Hermenegildo Garcia, *Angew. Chem. Int. Ed.* 2016, 55, 5414-5445

[5] Yabing He, Wei Zhou, Guodong Qian and Banglin Chen, *Chem. Soc. Rev.*, 2014, 43, 5657-5678

[6] Ben Van de Voorde, Bart Bueken, Joeri Denayer and Dirk De Vos, Chem. Soc. Rev., 2014, 43, 5766-5788

[7] a) Ha L. Nguyen, Felipe Gandara, Hiroyasu Furukawa, Tan L. H. Doan, Kyle E. Cordova, and Omar M. Yaghi, *J. Am. Chem. Soc.* 2016, 138, 4330-4333; b) Valentina G. Ponomareva, Konstantin A. Kovalenko, Alexei P. Chupakhin, Danil N. Dybtsev, Elena S. Shutova, and Vladimir P. Fedin, J. *Am. Chem. Soc.* 2012, 134, 15640-15643

[8] Vitalie Stavila, A. Alec Talin and Mark D. Allendorf, *Chem. Soc. Rev.*, 2014, 43, 5994-6010

[9] Zhichao Hu, Benjamin J. Deibert and Jing Li, *Chem. Soc. Rev.*, 2014, 43, 5815-5840

[10] Patricia Horcajada, Ruxandra Gref, Tarek Baati, Phoebe K. Allan, Guillaume Maurin, Patrick Couvreur, Gérard Férey, Russell E. Morris, and Christian Serre, *Chem. Rev.*, 2012, 112, 1232-1268

[11] Y. K. Hwang, D.-Y. Hong, J. S. Chang, S. H. Jhung, Y.-K. Seo, J. Kim, A. Vimont, M. Daturi, C. Serre, and G. Ferey, *Angew. Chem. Int. Ed*, 47, 2008, 4144

[12] 1) Y. Lee, S. Kim, J. K. Kang, S. M. Cohen, *Chem. Commun.*, 2015, 51, 5735; 2) M. Kim, J. F. Cahill, H. Fei, K. A. Prather, S. M. Cohen, *J. Am. Chem. Soc.* 2012, 134, 18082-18088

The invention claimed is:

1. A crystalline titanium-based inorganic-organic hybrid metal-organic framework (MOF) material constituted of a three-dimensional succession of building units of formula I$_0$:

$$M_aO_bL_xA_y \cdot n\text{Solv} \qquad (I_0)$$

wherein in each building unit, each occurrence of M independently represents Ti or another metal; wherein at least 60% of M atoms in the MOF material are Ti atoms;

each occurrence of L independently represents a bis-$C_6$aryl-containing tetracarboxylate ligand;

each occurrence of A independently represents a ligand comprising $HCO_2^-$ or $MeCO_2^-$; wherein at least one occurrence of A ligands in the MOF material may be replaced by ligands independently comprising $OH^-$, $H_2O$, $R^2-(SO_3)^-$, $R^2-(PO_3)H^-$, wherein $R^2$, for each occurrence, independently represents OH, $C_{1-12}$alkyl, $C_{1-12}$heteroalkyl, $C_{6-10}$aryl, $C_{5-10}$heteroaryl; where each of the foregoing alkyl and heteroalkyl moiety may be linear or branched and cyclic or acyclic;

a represents the number of M atoms in the building unit;
b represents the number of O atoms in the building unit;
x represents the number of L ligands in the building unit;
y represents the number of A ligands in the building unit;
n represents the average number of solvent molecules "Solv" coordinated to the metal centers M per building unit in the MOF material;

and b>a.

2. A crystalline MOF material according to claim 1, wherein the ratio b:a is ≥1.1.

3. A crystalline MOF material according to claim 1, wherein all occurrences of A independently represent a ligand comprising $HCO_2^-$ or $MeCO_2^-$.

4. A crystalline MOF material according to claim 1, wherein each occurrence of L independently represent a bis-$C_6$aryl-containing tetracarboxylate ligand of formula (II):

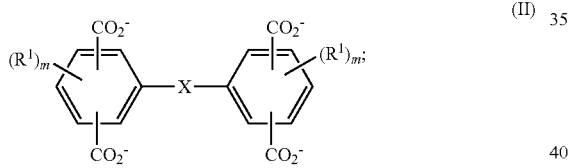

(II)

wherein X represents a covalent bond, C=O, $CH_2$, N=N, NH, O, S, $SO_2$, C=C, $-O-(CH_2)_p-O-$, $-NH-(CH_2)_p-NH-$ or $-S-(CH_2)_p-S-$ where p represents an integer ranging from 1 to 4; and each occurrence of m independently represents an integer from 1 to 3; and each occurrence of $R^1$ independently represents H, a halogen atom, OH, $NH_2$, $NO_2$ or a $C_{1-6}$alky; wherein when X is N=N or C=C, the at least one bis-$C_6$aryl-containing tetracarboxylate ligand of formula (II) may be of conformation cis or trans.

5. A crystalline MOF material according to claim 1, wherein each occurrence of L independently represent a bis-$C_6$aryl-containing tetracarboxylate ligand of any one of formulae ($II_1$) through ($II_{16}$):

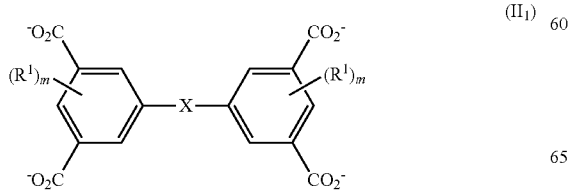

($II_1$)

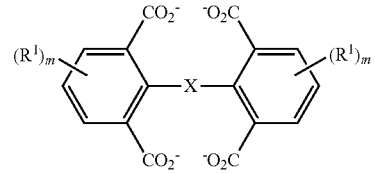

($II_2$)

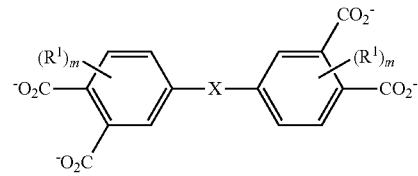

($II_3$)

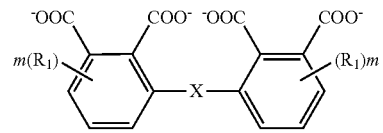

($II_4$)

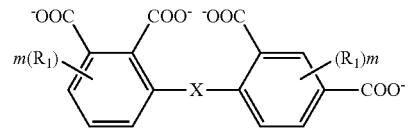

($II_5$)

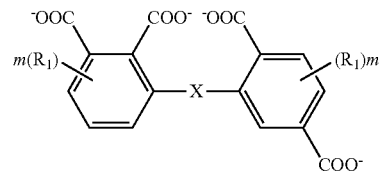

($II_6$)

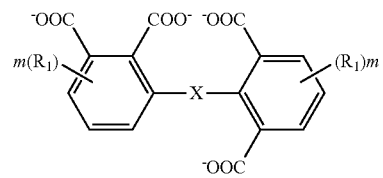

($II_7$)

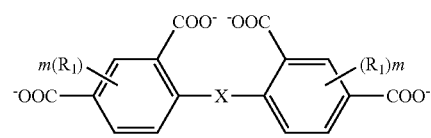

($II_8$)

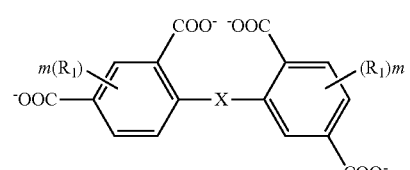

($II_9$)

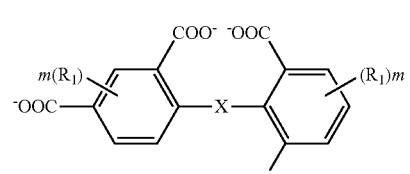

($II_{10}$)

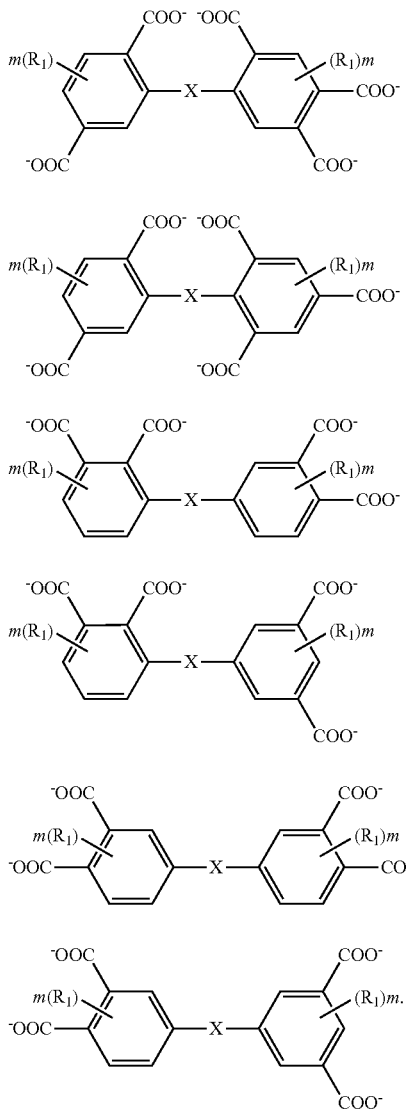

6. A crystalline MOF material according to claim 1, wherein each occurrence of L independently represent a bis-$C_6$aryl-containing tetracarboxylate ligand of any one of the following structures:

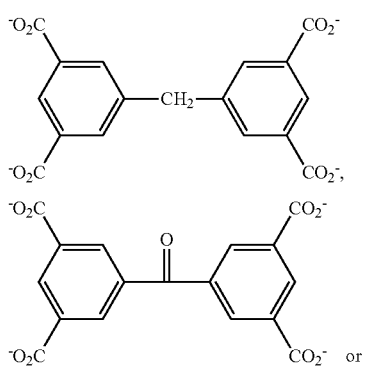

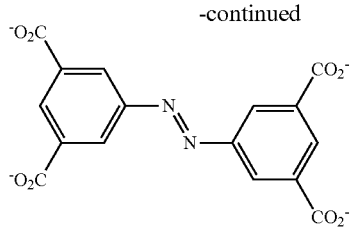

7. A crystalline MOF material according to claim 1, wherein the titanium-based inorganic-organic hybrid solid material is constituted exclusively of a three-dimensional succession of building units of formula (I) below:

$$Ti_{12}O_xL_3A_y \qquad (I)$$

wherein each occurrence of L independently represents a bis-$C_6$aryl-containing tetracarboxylate ligand having the structure of formula (II):

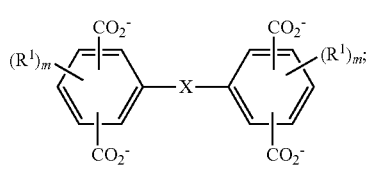

wherein X represents a covalent bond, C=O, $CH_2$, N=N, NH, O, S, $SO_2$, C=C, —O—$(CH_2)_p$—O—, —NH—$(CH_2)_p$—NH— or —S—$(CH_2)_p$—S— where p represents an integer ranging from 1 to 4;

each occurrence of m independently represents an integer from 1 to 3; and each occurrence of $R^1$ independently represents H, a halogen atom, OH, $NH_2$, $NO_2$ or a $C_{1-6}$alkyl;

each occurrence of A independently represents a ligand comprising $HCO_2^-$, $MeCO_2^-$, $OH^-$, $H_2O$, $R^2$—$(SO_3)^-$, $R^2$—$(PO_3)H^-$, wherein $R^2$, for each occurrence, independently represents OH, $C_{1-12}$alkyl, $C_{1-12}$heteroalkyl, $C_{6-10}$aryl, $C_{5-10}$heteroaryl; where each of the foregoing alkyl and heteroalkyl moiety may be linear or branched and cyclic or acyclic;

b represents 15 or 18;

y represents 0 or 6;

the titanium atoms form a purely inorganic elementary building block constituted of titanium oxo complexes; wherein the units of formula (I) together form a three-dimensional structure that crystallizes in the hexagonal crystal system; and wherein the building unit optionally further comprises water molecules coordinated to titanium metal centers of the building units.

8. A crystalline MOF material according to claim 7, wherein when y is 0 or 6 and A represents a formate ligand $HCO_2^-$, the crystal topology shall be related to an hexagonal crystal system and the P6/mmm space group or a sub-group or a multiple unit cell while retaining the initial topology.

9. A crystalline MOF material according to claim 7, wherein the three-dimensional structure of building units of formula (I) define cavities having a free diameter between 3 and 13 Å that are accessible through apertures having dimensions of 3 to 13 Å.

10. A crystalline MOF material according to claim 1, wherein the building units of the material have the formula (I⁴):

$$Ti_{12}O_{15}L_3A_6 \cdot nH_2O \qquad (I^4)$$

wherein
each occurrence of L independently represents a bis-$C_6$aryl-containing tetracarboxylate ligand having the structure of formula (II):

$$(II)$$

(R¹)ₘ–[benzene ring with CO₂⁻ groups]–X–[benzene ring with CO₂⁻ groups]–(R¹)ₘ;

wherein X represents a covalent bond, C=O, CH₂, N=N, NH, O, S, SO₂, C≡C, —O—(CH₂)ₚ—O—, —NH—(CH₂)ₚ—NH— or —S—(CH₂)ₚ—S— where p represents an integer ranging from 1 to 4;
each occurrence of m independently represents an integer from 1 to 3; and each occurrence of R¹ independently represents H, a halogen atom, OH, NH₂, NO₂ or a $C_{1-6}$alkyl;
each occurrence of A independently represents a ligand comprising HCO₂⁻MeCO₂⁻, OH⁻, H₂O, R²—(SO₃)⁻, R²—(PO₃)H⁻, wherein R², for each occurrence, independently represents OH, $C_{1-12}$alkyl, $C_{1-12}$heteroalkyl, $C_{6-10}$aryl, $C_{5-10}$heteroaryl; where each of the foregoing alkyl and heteroalkyl moiety may be linear or branched and cyclic or acyclic;
and n represents the average number of water molecules that are coordinated to the titanium metal centers per building unit in the material.

11. A crystalline MOF material according to claim 1, wherein the building units of the material have the formula (I^B):

$$Ti_{12}O_{18}L_3 \qquad (I^B)$$

wherein
each occurrence of L independently represents a bis-$C_6$aryl-containing tetracarboxylate ligand having the structure of formula (II):

$$(II)$$

(R¹)ₘ–[benzene ring with CO₂⁻ groups]–X–[benzene ring with CO₂⁻ groups]–(R¹)ₘ;

wherein X represents a covalent bond, C=O, CH₂, N=N, NH, O, S, SO₂, C≡C, —O—(CH₂)ₚ—O—, —NH—(CH₂)ₚ—NH— or —S—(CH₂)ₚ—S— where p represents an integer ranging from 1 to 4;
each occurrence of m independently represents an integer from 1 to 3; and each occurrence of R¹ independently represents H, a halogen atom, OH, NH₂, NO₂ or a $C_{1-6}$alkyl.

12. A crystalline MOF material according to claim 1, wherein the material has a BET specific surface area ranging from 100 to 2000 m²/g.

13. A crystalline MOF material according to claim 1, wherein the material has a pore volume of 0.1 to 1.5 cm³/g.

14. A crystalline MOF material according to claim 1, wherein the material is doped with one or more metals.

15. A process for preparing a crystalline titanium-based inorganic-organic hybrid MOF material as defined in claim 1, comprising at least one reaction step (i) of reacting in a suitable solvent system:
at least one titanium precursor comprising TiCl₄, TiO(acac)₂, TiOSO₄ (titanyl sulfate), Ti(SO₄)₂ or titanium alkoxides of formula (III):

$$Ti(OR^3)_4 \qquad (III)$$

wherein each occurrence of R³ independently represents a linear or branched $C_{1-6}$alkyl moiety;
formic acid or acetic acid or acetic anydride; and
a bis-$C_6$aryl-containing tetradentate ligand precursor having four —C(=O)R₄ moieties:
wherein each occurrence of R⁴ independently represents —OH, —OM₀ where M₀ represents an akali metal cation, a halogen atom, or a —OR⁵, —O—C(=O)R⁵ or —NR⁵R⁵' moiety, wherein R⁵ and R⁵' independently represent $C_{1-12}$alkyl;
wherein acac represents an acetylacetone ligand

[structure of acetylacetonate anion]

16. A process according to claim 15, wherein step (i) is carried out
A) by first mixing (i) formic acid, acetic acid or acetic anhydride, and (ii) the bis-$C_6$aryl-containing tetradentate ligand precursor either as such or in a suitable solvent; then adding (iii) the titanium precursor comprising TiCl₄, TiO(acac)₂, TiOSO₄ (titanyl sulfate), Ti(SO₄)₂ or a titanium alkoxide of formula (III) portion-wise (in several batches); followed by vigorous stirring and heating at a temperature between 100-150° C. for a suitable amount of time;
B) by successively adding (i) the bis-$C_6$aryl-containing tetradentate ligand precursor, (ii) the titanium precursor comprising TiCl₄, TiO(acac)₂, TiOSO₄ (titanyl sulfate), Ti(SO₄)₂ or a titanium alkoxide of formula (III), and then (iii) formic acid, acetic acid or acetic anhydride; followed by heating at a temperature between 80-120° C. for a suitable amount of time; or
C) under $1.10^5$ Pa (ambient pressure conditions) by successively adding (i) the bis-$C_6$aryl-containing tetradentate ligand precursor, (ii) formic acid, acetic acid or acetic anhydride, and then (iii) the titanium precursor comprising TiCl₄, TiO(acac)₂, TiOSO₄ (titanyl sulfate), Ti(SO₄)₂ or a titanium alkoxide of formula (III); and let the reaction proceed at a temperature ranging between 25° C.±3° C. (room temperature) and the boiling temperature of the mixture (reflux) for a suitable amount of time;
wherein acac represents an acetylacetone ligand

[structure of acetylacetonate anion]

17. A process according to claim 15, wherein the bis-$C_6$aryl-containing tetradentate ligand precursor has the structure:

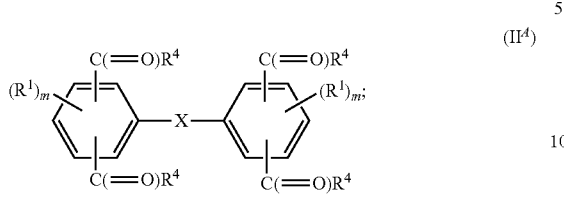

wherein X represents a covalent bond, C=O, $CH_2$, N=N, NH, O, S, $SO_2$, C=C, —O—$(CH_2)_p$—O—, —NH—$(CH_2)_p$—NH— or —S—$(CH_2)_p$—S— where p represents an integer ranging from 1 to 4;

each occurrence of m independently represents an integer from 1 to 3; and each occurrence of $R^1$ independently represents H, a halogen atom, OH, $NH_2$, $NO_2$ or a $C_{1-6}$alkyl; and each occurrence of $R^4$ independently represents —OH, —$OM_0$ where $M_0$ represents an akali metal cation, a halogen atom, or a —$OR^5$, —O—C(=O)$R^5$ or —$NR^5R^{5'}$ moiety, wherein $R^5$ and $R^{5'}$ independently represent $C_{1-12}$alkyl.

18. A process according to claim 15, wherein the precursor of formula (III) is comprises titanium ethoxide, titanium isopropoxide, titanium n-propoxide or titanium butoxide.

19. A process according to claim 15, wherein the crystalline titanium-based inorganic-organic hybrid MOF material obtained in step (i) is composed of a three-dimensional succession of building units of formula ($I^4$):

$$Ti_{12}O_{15}L_3A_6 \cdot nH_2O \qquad (I^4)$$

wherein A represents a formate ligand $HCO_2^-$ or an acetate ligand $MeCO_2^-$; n represents the average number of water molecules that are coordinated to the titanium metal centers per building unit in the material; and L represents a bis-$C_6$aryl-containing tetracarboxylate ligand having the structure (II):

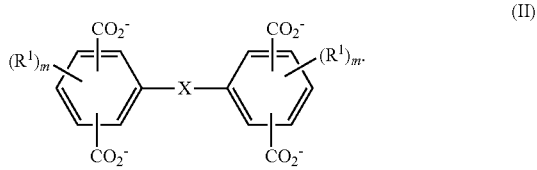

20. A process according to claim 19, further comprising a step of isolating the titanium-based inorganic-organic hybrid MOF material resulting from step (i) composed of a three-dimensional succession of building units of formula ($I^4$), and subjecting it to heat treatment at a temperature of 180-320° C. to form a titanium-based inorganic-organic hybrid solid material composed of a three-dimensional succession of building units of formula ($I^B$):

$$Ti_{12}O_{18}L_3 \qquad (I^B)$$

wherein L represents a bis-$C_6$aryl-containing tetracarboxylate ligand having the structure of formula (II).

21. A process according to claim 15, further comprising a step of isolating the resulting titanium-based inorganic-organic hybrid MOF material and:

(a) reacting it with HCl, $H_2SO_4$, $H_3PO_4$, $R^2$—$SO_3H$, or $R^2$—$PO_3H_2$, wherein $R^2$, for each occurrence, independently represent OH, $C_{1-12}$alkyl, $C_{1-12}$heteroalkyl, $C_{6-10}$aryl, $C_{5-10}$heteroaryl; where each of the foregoing alkyl and heteroalkyl moiety may be linear or branched and cyclic or acyclic; or (b) subjecting it to vacuum at a temperature ranging from 20 to 200° C. and subsequently exposing the resulting material to air moisture at a temperature from 20 to 100° C. to replace the formate or acetate ligands in the MOF lattice with OH/$H_2O$ ligands; or (c) subjecting it to vacuum at a temperature ranging from 20 to 200° C. and subsequently exposing the resulting material to a vaporized organic compound at temperature below its boiling temperature to replace the formate or acetate ligands in the MOF lattice with other organic ligands; or (d) subjecting it to solvothermal treatment in the presence of molecules having a polar complexing group to replace the formate or acetate ligands on the metal centers.

22. A process of according to claim 15, wherein, prior to adding the titanium precursor comprising $TiCl_4$, $TiO(acac)_2$, $TiOSO_4$ (titanyl sulfate), $Ti(SO_4)_2$ or a titanium alkoxide of formula (III), another metallic inorganic precursor in the form of a metal $M_1$, a salt of a metal $M_1$ of formula (IV) or a hydroxide or oxide of a metal $M_1$, is added to the reaction mixture;

$$M_1Y_p \cdot nH_2O \qquad (IV)$$

wherein $M_1$ is a metal comprising Cu, Fe, Co, Ni, Mn, V, Cr, Ru, Sn or Nb; and Y represents $Cl^-$, $NO_3^-$, $SO_4^{2-}$, $AcO^-$, or

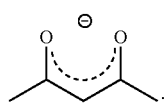.

23. A material as defined in claim 1, configured as a catalyst support for carrying out heterogeneously catalyzed chemical reactions, or as a gas storage/separation/purification material, or as a matrix for encapsulating active principles, or as a photochromic material for information storage, laser printing or as an oxygen indicator, or as proton conductive material, or a optoelectronic material, or as a sensing material.

24. A crystalline titanium-based inorganic-organic hybrid MOF material having an oxo to metal ratio >1.0 wherein at least 60% of metal atoms in the MOF material are Ti atoms; obtainable by a process comprising at least one reaction step (i) of reacting in a suitable solvent system:

at least one titanium precursor comprising $TiCl_4$, TiO$(acac)_2$, $TiOSO_4$ (titanyl sulfate), $Ti(SO_4)_2$ or titanium alkoxides of formula (III):

$$Ti(OR^3)_4 \qquad (III)$$

wherein each occurrence of $R^3$ independently represents a linear or branched $C_{1-6}$alkyl moiety;

formic acid or acetic acid or acetic anydride; and a bis-$C_6$aryl-containing tetradentate ligand precursor having four —C(=O)$R_4$ moieties: wherein each occurrence of $R^4$ independently represents —OH, —$OM_0$ where $M_0$ represents an akali metal cation, a halogen atom, or a —OR$^5$, —O—C(=O)R$^5$ or —NR$^5$R$^{5'}$ moiety, wherein R$^5$ and R$^{5'}$ independently represent C$_{1-12}$alkyl;
wherein acac represents an acetylacetone ligand
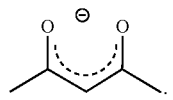
(5)
(10)
* * * * *